United States Patent
Sperl et al.

(10) Patent No.: US 12,364,680 B2
(45) Date of Patent: *Jul. 22, 2025

(54) COMPOUNDS FOR TREATING OPHTHALMIC DISEASES AND DISORDERS

(71) Applicant: KIORA PHARMACEUTICALS GmbH, Vienna (AT)

(72) Inventors: Stefan Sperl, Vienna (AT); Franz Obermayr, Vienna (AT)

(73) Assignee: KIORA PHARMACEUTICALS GmbH, Vienna (AT)

( * ) Notice: Subject to any disclaimer, the term of this patent is extended or adjusted under 35 U.S.C. 154(b) by 110 days.

This patent is subject to a terminal disclaimer.

(21) Appl. No.: 18/189,010

(22) Filed: Mar. 23, 2023

(65) Prior Publication Data

US 2023/0285355 A1   Sep. 14, 2023

Related U.S. Application Data

(63) Continuation of application No. 15/309,176, filed as application No. PCT/EP2015/060166 on May 8, 2015, now Pat. No. 11,730,716.

(30) Foreign Application Priority Data

May 8, 2014 (EP) .................................... 14167490
May 30, 2014 (EP) .................................... 14170616

(51) Int. Cl.
*A61K 31/381* (2006.01)
*A61K 9/00* (2006.01)
(Continued)

(52) U.S. Cl.
CPC .......... *A61K 31/381* (2013.01); *A61K 9/0048* (2013.01); *A61K 31/196* (2013.01);
(Continued)

(58) Field of Classification Search
CPC ...... A61K 31/277; A61K 31/47; A61K 47/32; A61K 31/42; A61K 47/10; A61K 31/44;
(Continued)

(56) References Cited

U.S. PATENT DOCUMENTS 6,743,826 B1   6/2004  Hegedus et al.
7,365,094 B2   4/2008  Leban et al.
(Continued)

FOREIGN PATENT DOCUMENTS

EP   0 179 477   4/1986
EP   0 413 329   2/1991
(Continued)

OTHER PUBLICATIONS

Appeal Brief; filed Jan. 27, 2022; U.S. Appl. No. 15/309,176.
(Continued)

*Primary Examiner* — Hong Yu
(74) *Attorney, Agent, or Firm* — Knobbe, Martens, Olson & Bear, LLP

(57) ABSTRACT

The present invention relates generally to the field of ocular therapeutics and the development thereof for use in humans or animals. More particularly, it relates to DHODH inhibitor compounds and their use for the treatment of ophthalmic diseases and disorders. The invention also relates to the local administration of such ophthalmic compositions, and in particular to their intravitreal administration. The invention relates also to controlled release formulations of therapeutically active agents, in particular of DHODH inhibitor compounds administered intraocularly, in particular in the posterior segment of the eye.

16 Claims, 4 Drawing Sheets

(51) Int. Cl.

| | |
|---|---|
| *A61K 31/196* | (2006.01) |
| *A61K 31/277* | (2006.01) |
| *A61K 31/341* | (2006.01) |
| *A61K 31/42* | (2006.01) |
| *A61K 31/44* | (2006.01) |
| *A61K 31/4418* | (2006.01) |
| *A61K 31/47* | (2006.01) |
| *A61K 31/4704* | (2006.01) |
| *A61K 47/10* | (2017.01) |
| *A61K 47/32* | (2006.01) |
| *A61K 47/38* | (2006.01) |

(52) U.S. Cl.
CPC .......... *A61K 31/277* (2013.01); *A61K 31/341* (2013.01); *A61K 31/42* (2013.01); *A61K 31/44* (2013.01); *A61K 31/4418* (2013.01); *A61K 31/47* (2013.01); *A61K 31/4704* (2013.01); *A61K 47/10* (2013.01); *A61K 47/32* (2013.01); *A61K 47/38* (2013.01)

(58) Field of Classification Search
CPC .. A61K 47/38; A61K 31/4418; A61K 9/0048; A61K 31/196; A61K 31/4704; A61K 31/341; A61K 31/381; A61P 37/06; A61P 43/00; A61P 27/02
See application file for complete search history.

(56) References Cited

U.S. PATENT DOCUMENTS

| | | | |
|---|---|---|---|
| 7,714,132 | B2 | 5/2010 | Fecher et al. |
| 8,354,433 | B2 | 1/2013 | Vitt et al. |
| 9,795,590 | B2 | 10/2017 | Strobl |
| 11,730,716 | B2 * | 8/2023 | Sperl .................... A61K 31/196 424/489 |
| 12,209,073 | B2 | 1/2025 | Sperl et al. |
| 2004/0176458 | A1 | 9/2004 | Leban et al. |
| 2004/0192758 | A1 | 9/2004 | Leban et al. |
| 2004/0254154 | A1 | 12/2004 | Ashton |
| 2010/0280081 | A1 | 11/2010 | Vitt et al. |
| 2011/0021465 | A1 | 1/2011 | Minatelli et al. |
| 2011/0275603 | A1 | 11/2011 | Muthuppalaniappan et al. |
| 2019/0025313 | A1 | 1/2019 | Si et al. |
| 2021/0052737 | A1 | 2/2021 | Sperl et al. |
| 2023/0278979 | A1 | 9/2023 | Sperl et al. |

FOREIGN PATENT DOCUMENTS

| | | |
|---|---|---|
| EP | 0 834 320 | 8/1998 |
| JP | 2006-089485 | 4/2006 |
| JP | 2009-270356 | 11/2009 |
| WO | WO 99/013914 | 3/1999 |
| WO | WO 2003/006425 | 1/2003 |
| WO | WO 2004/056746 | 7/2004 |
| WO | WO 2004/056747 | 7/2004 |
| WO | WO 2004/056797 | 7/2004 |
| WO | WO 2006/022442 | 3/2006 |
| WO | WO 2007/038687 | 4/2007 |
| WO | WO 2008/077639 | 7/2008 |
| WO | WO 2009/021696 | 2/2009 |
| WO | WO 2010/128050 | 11/2010 |
| WO | WO 2011/138665 | 11/2011 |
| WO | WO 2015/154820 | 10/2015 |
| WO | WO 2022/214691 | 10/2022 |

OTHER PUBLICATIONS

Examiner's Answer to Appeal Brief; Mailed Apr. 6, 2022; U.S. Appl. No. 15/309,176.
Reply Brief; filed Jun. 3, 2022; U.S. Appl. No. 15/309,176.
Affidavit/Declaration/ Exhibit After Notice of Appeal; filed Dec. 2, 2022; U.S. Appl. No. 15/309,176.
Patent Board Decision—Examiner Reversed; Mailed Dec. 21, 2022; U.S. Appl. No. 15/309,176.
Notice of Allowance and Fees Due (PTOL-85); Mailed Mar. 8, 2023; U.S. Appl. No. 15/309,176.
Castiblanco et al., 2014, Review of systemic immunosuppression for autoimmune uveitis, Ophthalmol Ther, 3:17-36.
Diedrichs-Mohring et al., 2018, Intraocular DHODH-inhibitor PP-001 suppresses relapsing experimental uveitis and cytokine production of human lymphocytes, but not of RPE cells J. of Neuroinflammation, 15(54):1-11.
Fang et al., Apr. 2013, Amelioration of Experimental Autoimmune Uveitis by Leflunomide in Lewis Rats, PLoS ONE 8(4):e62071.
Kompella at el., 2011, Drug Product Development for the Back of the Eye, Springer, New York (TOC).
Marschall et al.,, 2013, Assessment of drug candidates for broad-spectrum antiviral therapy targeting cellular pyrimidine biosynthesis, Antiviral Research, 100(3):640-648 with supporting information.
Peyman et al., 2009, Intravitreal injection of therapeutic agents, retrieved from internet: https://insights.ovid.com/pubmed?pmid=19584648, 1 p.
Suhler et al., Jul. 2018, Safety and Efficacy of Adalimumab in Patients with Noninfectious Uveitis in an Ongoing Open-Label Study: Visual III, Ophthalmology, 125(7):1075-1087.
Sung et al., 1999, Intravitreal controlled release implant for leflunomide: Potential treatment for uveitis, Proceedings of he International Symposium on Controlled Release of Bioactive Materials, 26:38-39.
Yeh et al., 2019, Suprachoroidal injection of triamcinolone acetonide, CLS-TA, for macular edema due to noninfectious uveitis, Retina 39(10):1880-1888.
Written Opinion for PCT/EP2015/060166 of Panoptes Pharma GES, M.B.H., (Dec. 11, 2015).
Berge et al., Jan. 1977, Pharmaceutical Salts, J. Pharm. Sci., 66(1):1-19.
Brittain, Dec. 1, 2009, Developing an appropriate salt form for an active pharmaceutical ingredient, American Pharmaceutical Review, 12(7):62-65.
CAS Registry No. 717142-73-9. Accessed Dec. 4, 2023, 2 pp.
Chong et al., 2006, Concurrent Antiviral and Immunosuppresive Activites of Leflunomide In Vivo, Am. J. Transplant, 5(1):69-75.
Kindsmuller et al., Sep. 2009, A 49-Kilodalton Isoform of the Adenovirus Type 5 Early Revion 1B 55-Kilodalton Protein Is Sufficient to Support Virus Replication, J. Viral. 83(18):9045-9056.
Klein, 2010, The use of biorelevant dissolution media to forecast the in vivo performance of a drug, The AAPS Journal, 12(3):397-406.
Marschall et al., 2012, In Vitro Evaluation of the Activies of the Novel Anticytomegalovirus Compound AIC246 letermovir) against Herpesviruses and other Human Pathogenic Viruses, Antimicrob. Agents Chemother. 56:1135-1137.
Meister, 2005, Antiviral Mechanism(s) of the Experimental Immunosuppressive Agent Leflunomide Against Human Cytomegalovirus and Polyomavirus, doctoral dissertation, Ohio State University, 141 pp.
Schuerer et al., May 7-11, 2017, Ocular toxicity and ocular tissue distribution of topically applied PP-001 in vivo, Abstract from the Annual Meeting of the Association for Research in Vision and Ophthalmology, Baltimore MD, 2 pp.
Shimmura et al., 2003, Albumin as a tear supplement in the treatment of sever dry eye, Br. J Ophthalmology, 87:1279-1283.
Supporting information for Marschall, Manfred, et al. "Assessment of Drug Candidates for Broad-Spectrum Antiviral Therapy Targeting Cellular Pyrimidine Biosynthesis." Antiviral Research, vol. 100, No. 3, Dec. 2013, pp. 640-648. ScienceDirect, https://doi.org/10.1016/j.antiviral.2013.10.003. (Year: 2013).
Yamasaki et al., 2013, Albumin-drug interaction and its clinical implication. Biochim Biophys Acta, 1830(12):543505443.
Baumgartner et al., 2006, Dual Binding Mode of a Novel Series of DHODH Inhibitors Journal of Medicinal Chemistry, 49(4):1239-1247.
Davis et al., 1996, The Immunosuppressive Metabolite of Leflunomide is a Potent Inhibitor of Human Dihydroorotate Dehydrogenase, Biochemistry, 35(4):1270-1273.

(56) References Cited

OTHER PUBLICATIONS

Leban et al., 2006, Biphenyl-4-ylcarbamoyl thiophene carboxylic acids as potent DHODH inhibitors, Bioorg Med Chem cell., 16(2):267-270.
Rechter et al., 2006, Antiviral activity of Arthrospira-derived spirulan-like substances, Antiviral Res. 72:197-206.

* cited by examiner

COMPOUNDS FOR TREATING OPHTHALMIC DISEASES AND DISORDERS

FIELD OF THE INVENTION

The present invention relates generally to the field of ocular therapeutics and the development thereof for use in humans or animals. More particularly, it relates to DHODH inhibitor compounds and their use for the treatment of ophthalmic diseases and disorders.

The invention also relates to the administration of such ophthalmic compositions, either for topical treatment or in particular to their intravitreal administration. The invention relates also to the controlled release of therapeutic active agents, in particular of DHODH inhibitor compounds intraocularly, in particular in the posterior segment of the eye.

BACKGROUND ART

Ocular surface diseases encompass a plethora of pathologies with overlapping conditions leading to common sequels: dysfunction of the ocular tear film and/or the integrity of the ocular surface. The ocular surface is richly innervated by sensory nerves, therefore, any stimulus that affects these tissues can lead to a variety of symptoms. These range from mild discomfort to grittiness, foreign body sensation, irritation, and dryness affecting the quality of life of millions. Furthermore inflammation can cause damage to the various structures of the ocular surface: i.e. scarring of tissues underlying the conjunctival epithelium and destruction of the Becher-cells leading to dry eyes and/or causing irregularity of the corneal surface that might result in glare. In severe cases, where the condition is chronic with surface damage, it might lead to mild to profound decreases in vision as seen in severe dry eyes syndromes, vernal keratoconjunctivitis or infectious diseases as trachoma.

Uveitis is an inflammatory and chronic disease of the eye affecting the uvea, the middle, pigmented layer of the eye. Apart from corticosteroids and immuno-suppressives no treatment is currently available. Both classes of drugs are known to cause serious side effects when used for a prolonged time period, needed to treat chronic uveitis. Such side effects include osteoporosis, extreme weight gain, diabetes etc. Autoimmune uveitis is associated with immunological response by T helper cells (Th1 and Th17) to human retinal or cross-reactive proteins. These autoreactive T helper cells migrate and infiltrate the eye and are the main cause of the inflammation of the eye. It has been shown in animal models and in humans that neutralizing these deregulated T cells (hallmark cytokines: IFN-γ for Th1 and IL-17 for Th17) lead to an amelioration of clinical uveitis.

Uveitis is one of the leading causes of blindness in the world and the fourth leading cause in the western world and several million patients suffer from any form of uveitis which can occur in any age group.

Conjunctivitis (often called "pink eye") is an inflammation of the conjunctiva, which is the mucous membrane covering the white part of the eye and the inner side of the eyelid.

The most common form of conjunctivitis is caused by adenoviral infection. This type of conjunctivitis may also spread to affect the cornea (keratitis), and may persist for several weeks and cause hazy vision. Since the disease is often epidemic in nature, it is called epidemic keratoconjunctivitis (EKC). EKC is a serious and contagious form of conjunctivitis (conjunctiva and cornea).

Symptoms of EKC include acute onset of watering redness, foreign body sensation and severe pain, diminished eyesight, tearing, and sensitivity to light. In approximately 20-50% of the patients, an immune T cell mediated infiltration of the corneal stroma that results in deteriorating vision is observed. Millions of patients suffer from viral conjunctivitis which can occur in any age group. Currently no antiviral treatment is available.

Therapeutic agents for treating ocular conditions are known, but typically those agents are associated with the development of one or more side-effects. For example, ocular corticosteroid treatment (Prednisolon or Dexamethason) can induce unwanted increases in intraocular pressure or prostaglandin treatments, e.g., PGF2, can induce hyperemia.

WO2007038687 disclose a method for minimizing systemic exposure to a steroid-sparing immunosuppressive agent by administering said agent directly into an eye of a subject having or at risk for having an ocular disease. EP0413329 describe the use of leflunomide for the treatment of ocular diseases with immune etiology.

DHODH inhibitors like leflunomide and teriflunomide are used systemically to treat diseases like rheumatoide arthritis and multiple sclerosis. Fang et al. described the systemic use of leflunomide to treat experimental autoimmune uveitis in rats (Fang C B, et al. (2013) Amelioration of Experimental Autoimmune Uveitis by Leflunomide in Lewis Rats. PLoS ONE 8(4): e62071). However, due to the active blood-ocular-barrier, high systemic drug exposure is needed to treat the eye disease uveitis. Since leflunomide is known to have the potential to cause severe liver toxicity, this approach would have a low risk-benefit ratio. Furthermore, it is generally favorable to avoid systemic drug exposure and potential systemic side effects in order to treat local eye diseases.

Because of the low safety of the existing therapeutics there is a high unmet medical need for a new and safer class of drugs to treat ocular diseases, in particular to treat uveitis and/or conjunctivitis.

SUMMARY OF INVENTION

The problem is solved by the present invention. It was surprisingly found by the inventors that DHODH inhibitor compounds are highly efficacious and well tolerated to treat eye diseases by local administration to the eye.

The present invention provides a method to treat an ocular disease or condition, wherein an effective amount of a DHODH inhibitor compound is locally administered to the eye of a subject in need thereof. Specifically, the method relates to a DHODH inhibitor compound for use in local drug delivery in a method to treat an ocular disease.

The ocular disease or condition to be treated can be uveitis, optic neuritis, retrobulbar neuritis, ocular inflammation or discomfort or trauma caused by or associated with the use of contact lenses, ocular inflammation, dry eye, discomfort or trauma caused by or associated with refractive surgery, macular degeneration, optionally radial keratotomy or astigmatic keratotomy, blepharitis, an optic nerve disease or disorder, optionally papilledema or a conjunctivitis condition, optionally allergic conjunctivitis, pink eye, giant papillary conjunctivitis, infectious conjunctivitis or chemical conjunctivitis.

without treatment of EAU in rats (placebo control) and effective prevention of relapses by treatment with the DHODH inhibitor PP-001. Treatment with placebo or PP-001 started on day 17 post immunization.

Figure 2:
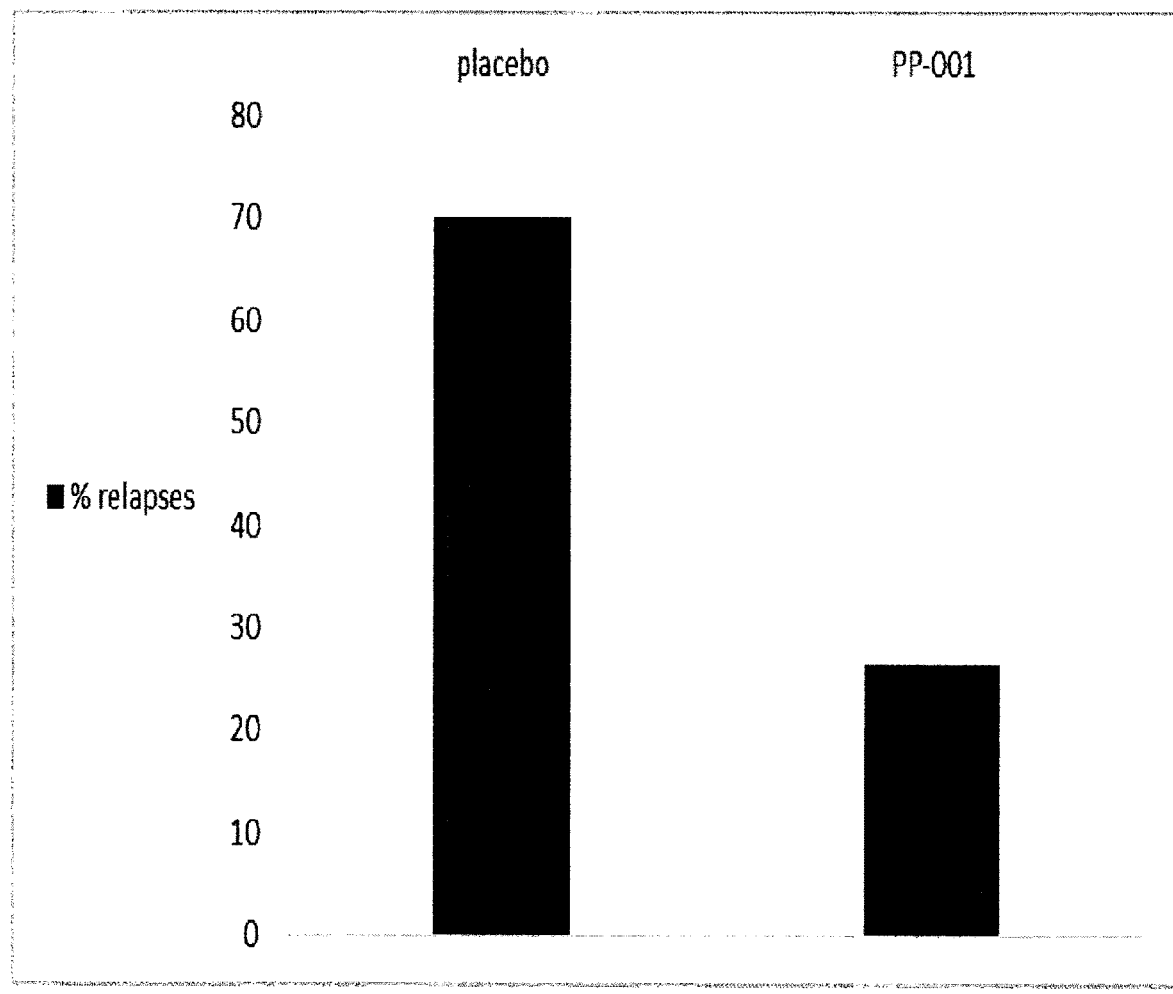

FIG. 2 describes the percentage of uveitis relapses in EAU rats after a single intravitreal injection with placebo and PP-001.

Figure 3:
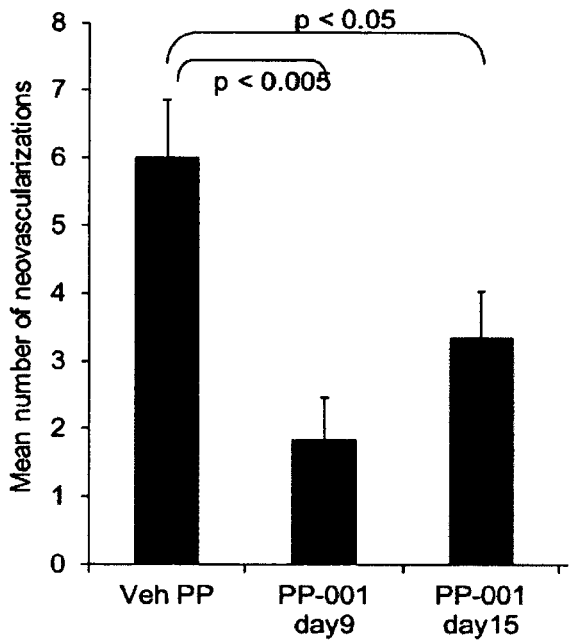

FIG. 3 describes the effect of PP-001 treatment on choroidal neovascularization in the EAU rat model. Treatment started on day 9 (onset of inflammation) or on day 15 (peak of inflammation) post immunization.

Figure 4:
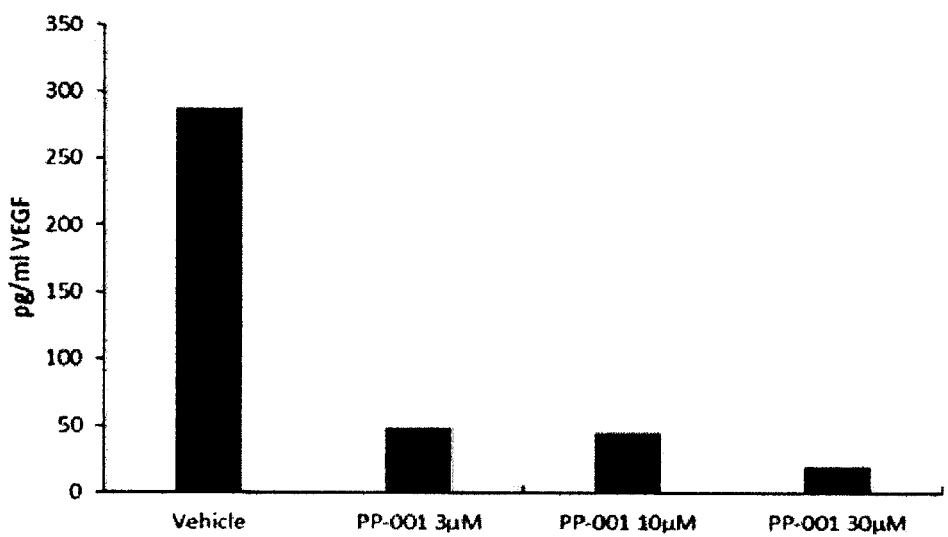

FIG. 4 describes the concentration-dependent inhibition of vascular endothelial growth factor (VEGF) by PP-001.

Figure 5:
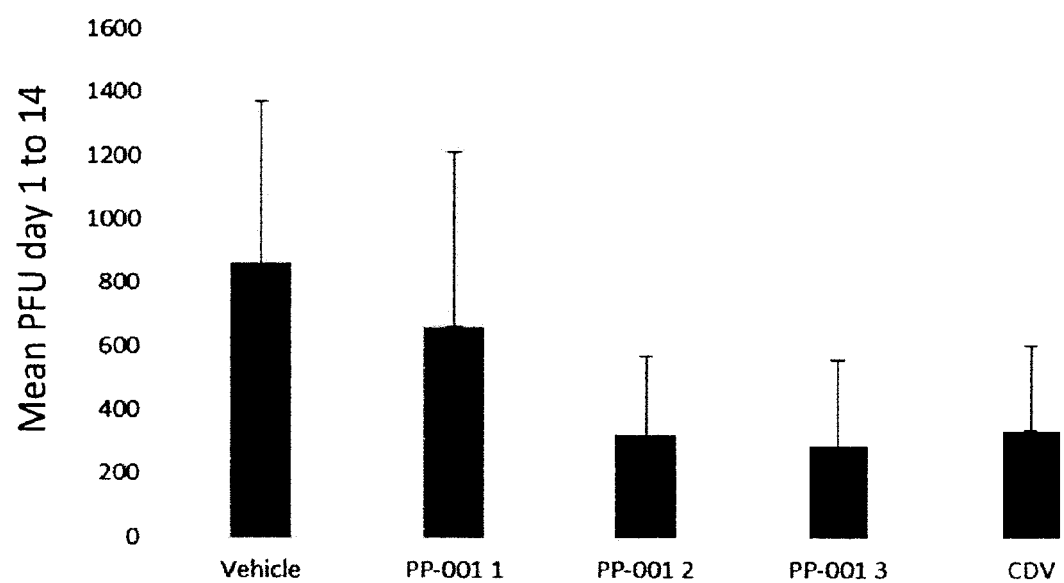

FIG. 5 shows the antiviral efficacy of PP-001 eye drops in an animal model. The viral titers during the treatment course are expressed as plaque-forming units.

Figure 6:
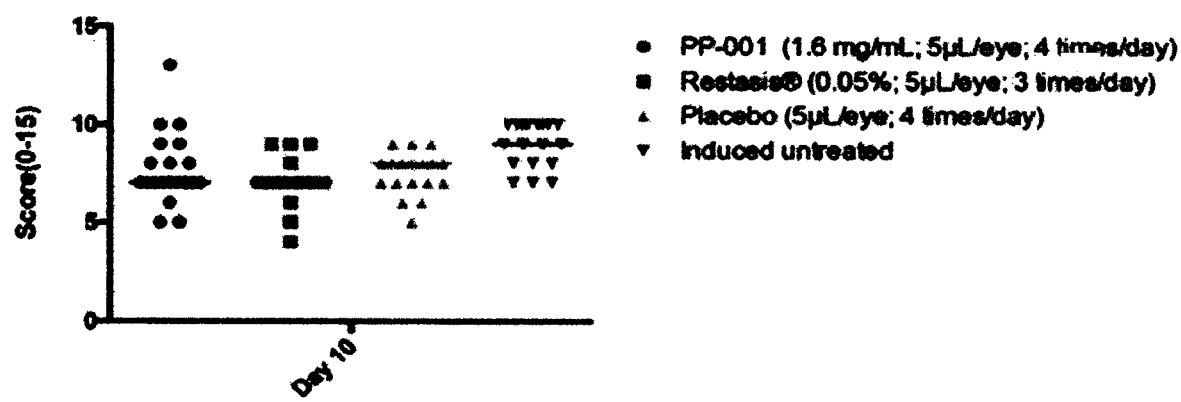

FIG. 6 shows the efficacy of topical administrations of PP-001 in a controlled-environment chamber murine model of dry eye.

DESCRIPTION OF EMBODIMENTS

It has been surprisingly found by the inventors that DHODH inhibitor compounds are effective in treating ocular diseases, conditions or symptoms related thereto by ameliorating inflammation and/or by increasing healing or repair of injured ocular tissue or cells. Enhanced cell or tissue repair would slow ocular disease progression, enhance recovery or render an existing disease (usually mild to moderate) sub-clinical or nearly sub-clinical.

Therefore the present invention relates to a DHODH inhibitor compound for use in local drug delivery in the treatment of an ocular disease.

The DHODH inhibitor compound is selected from the group consisting of leflunomide, teriflunomide, vidofludimus, brequinar, ASLAN003 or a compound of general formula I, $$(R^1)_t \overset{X}{\underset{A}{\bigcirc}} L \overset{Z^2}{\underset{\parallel}{\stackrel{\parallel}{C}}} N \overset{}{\underset{R^8}{\stackrel{}{\longrightarrow}}} E - [D_m - (CHR^3)_n]_q - Y$$
$$\phantom{xxxxxxxxxxxxxxx} \underset{Z^1}{\overset{\parallel}{C}} R^2$$

wherein
A is an aromatic or non-aromatic 5- or 6-membered hydrocarbon ring wherein optionally one or more of the carbon atoms are replaced by a group X, wherein X is independently selected from the group consisting of S, O, N, $NR^4$, $SO_2$ and SO;
L is a single bond or NH;
D is O, S, $SO_2$, $NR^4$, or $CH_2$;
$Z^1$ is O, S, or $NR^5$;
$Z^2$ is O, S, or $NR^5$;
$R^1$ independently represents H, halogen, haloalkanyl, haloalkenyl, haloalkynyl, haloalkanyloxy, haloalkenyloxy, haloalkynyloxy, —$CO_2R''$, —$SO_3H$, —OH, —$CONR*R''$, —CR"O, —$SO_2$—$NR*R''$, —$NO_2$, —$SO_2$—R", —SO—R*, —CN, alkanyloxy, alkenyloxy, alkynyloxy, alkanylthio, alkenylthio, alkynylthio, aryl, —NR"—$CO_2$—R', —NR"—CO—R*, —NR"—$SO_2$—R', —O—CO—R*, —O—$CO_2$—R*, —O—CO—NR*R", cycloalkyl, heterocycloalkyl, alkanylamino, alkenylamino, alkynylamino, hydroxyalkanylamino, hydroxyalkenyl-amino, hydroxyalkynylamino, —SH, heteroaryl, alkanyl, alkenyl or alkynyl;

R* independently represents H, alkanyl, alkenyl, alkynyl, cycloalkyl, heterocyclo-alkyl, aminoalkanyl, aminoalkenyl, aminoalkynyl, alkanyloxy, alkenyloxy, alkynyloxy, —OH, —SH, alkanylthio, alkenylthio, alkynylthio, hydroxyalkanyl, hydroxyalkenyl, hydroxyalkynyl, haloalkanyl, haloalkenyl, haloalkynyl, haloalkanyloxy, haloalkenyloxy, haloalkynyloxy, aryl or heteroaryl;

R' independently represents H, —$CO_2R''$, —$CONR''R'''$, —CR"O, —$SO_2NR''$, —NR"—CO-haloalkanyl, haloalkenyl, haloalkynyl, —$NO_2$, —NR"—$SO_2$-haloalkanyl, haloalkenyl, haloalkynyl, —NR"—$SO_2$-alkanyl, —NR"—$SO_2$-alkenyl, —NR"—$SO_2$-alkynyl, —$SO_2$-alkanyl, —$SO_2$-alkenyl, —$SO_2$-alkynyl, —NR"—CO-alkanyl, —NR"—CO-alkenyl, —NR"—CO-alkynyl, —CN, alkanyl, alkenyl, alkynyl, cycloalkyl, heterocycloalkyl, aminoalkanyl, aminoalkenyl, aminoalkynyl, alkanylamino, alkenylamino, alkynylamino, alkanyloxy, alkenyloxy, alkynyloxy, cycloalkyloxy, —OH, —SH, alkanylthio, alkenylthio, alkynylthio, hydroxyalkanyl, hydroxyalkenyl, hydroxyalkynyl, hydroxyalkanylamino, hydroxyalkenyl-amino, hydroxyalkynylamino, halogen, haloalkanyl, haloalkenyl, haloalkynyl, haloalkanyloxy, haloalkenyloxy, haloalkynyloxy, aryl, aralkyl or heteroaryl;

R" independently represents hydrogen, haloalkanyl, haloalkenyl, haloalkynyl, hydroxyalkanyl, hydroxyalkenyl, hydroxyalkynyl, alkanyl, alkenyl, alkynyl, cycloalkyl, heterocycloalkyl, aryl, heteroaryl, aminoalkanyl, aminoalkenyl or aminoalkynyl;

R''' independently represents H or alkanyl;

$R^2$ is H or $OR^6$, $NHR^7$, $NR^7OR^7$;

or $R^2$ together with the nitrogen atom which is attached to $R^8$ forms a 5 to 7 membered, preferably 5 or 6 membered heteroyclic ring wherein $R^2$ is —$[CH_2]_8$ and $R^8$ is absent;

$R^3$ is H, alkanyl, alkenyl, alkynyl, cycloalkyl, heterocycloalkyl, aryl, alkanyloxy, alkenyloxy, alkynyloxy, —O-aryl; —O-cycloalkyl, —O-heterocycloalkyl, halogen, amino-alkanyl, aminoalkenyl, aminoalkynyl, alkenylamino, alkenylamino, alkynylamino, hydroxylamino, hydroxylalkanyl, hydroxylalkenyl, hydroxylalkynyl, haloalkanyloxy, haloalkenyloxy, haloalkynyloxy, heteroaryl, alkanylthio, alkenylthio, alkynylthio, —S-aryl; —S-cycloalkyl, —S-heterocycloalkyl, aralkyl, haloalkanyl, haloalkenyl or haloalkynyl;

$R^4$ is H, alkanyl, alkenyl, alkynyl, cycloalkyl, heterocycloalkyl, aryl or heteroaryl;

$R^5$ is H, OH, alkanyloxy, alkenyloxy, alkynyloxy, O-aryl, alkanyl, alkenyl, alkynyl or aryl;

$R^6$ is H, alkanyl, alkenyl, alkynyl, cycloalkyl, heterocycloalkyl, aryl, heteroaryl, aralkyl, alkanyloxyalkanyl, alkanyloxyalkenyl, alkanyloxyalkynyl, alkenyloxyalkanyl, alkenyloxyalkenyl, alkenyloxyalkynyl, alkynyloxyalkanyl, alkynyloxyalkenyl, alkynyloxyalkynyl, acylalkanyl, (acyloxy)alkanyl, (acyloxy)alkenyl, (acyloxy)alkynyl acyl, non-symmetrical (acyloxy)alkenyldiester, non-symmetrical (acyloxy)alkenyldiester, non-symmetrical (acyloxy)alkynyldiester, or dialkanylphosphate, dialkenylphosphate or dialkynylphosphate;

R[7] is H, OH, alkanyl, alkenyl, alkynyl, aryl, alkanyloxy, alkenyloxy, alkynyloxy, —O-aryl, cycloalkyl, heterocycloalkyl, —O-cycloalkyl, or —O-heterocycloalkyl;

R[8] is H, alkanyl, alkenyl or alkynyl;

E is an alkanyl, alkenyl, alkynyl, aryl, heteroaryl, heterocycloalkyl or cycloalkyl group or a fused bi- or tricyclic ring system wherein one phenyl ring is fused to one or two monocyclic cycloalkyl or heterocycloalkyl rings or one bicyclic cycloalkyl or heterocycloalkyl ring, or wherein two phenyl rings are fused to a monocyclic cycloalkyl or heterocycloalkyl ring, wherein monocyclic and bicyclic cycloalkyl and heterocyclo-alkyl rings are as defined herein, and wherein all of the aforementioned groups may optionally be substituted by one or more substituents R';

Y is H, halogen, haloalkanyl, haloalkenyl, haloalkynyl, haloalkanyloxy, haloalkenyloxy, haloalkynyloxy, alkanyl, alkenyl, alkynyl, aryl, heteroaryl, heterocycloalkyl or cycloalkyl group or a fused bi- or tricyclic ring system wherein one phenyl ring is fused to one or two monocyclic cycloalkyl or heterocycloalkyl rings or one bicyclic cycloalkyl or heterocycloalkyl ring, or wherein two phenyl rings are fused to a monocyclic cycloalkyl or heterocycloalkyl ring, and wherein all of the aforementioned groups may optionally be substituted by one or more substituents R', or Y is

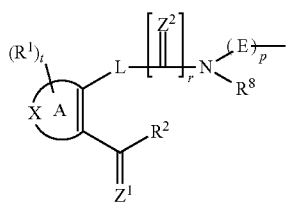

wherein R[1], X, A, Z[1], Z[2], R[8], R[2], E and p are as defined herein;

m is 0 or 1;
n is 0 or 1;
p is 0 or 1;
q is 0 or 1;
r is 0 or 1;
s is 0 to 2; and
t is 0 to 3.

Specifically, the DHODH inhibitor compound according to the invention is a compound of general formula I, wherein A is furan, thiophene, pyridyl, phenyl; dihydrothiophene, cyclopentenyl or cyclopentadienyl and the other residues are as defined above.

A further embodiment of the invention is the DHODH inhibitor compound of general formula I, wherein A is thiophene and the other residues are as defined above.

A further embodiment of the invention is the DHODH inhibitor compound of general formula I, wherein Z[1] and Z[2] are O.

A further embodiment of the invention is the DHODH inhibitor compound of general formula I, wherein E is phenyl optionally substituted by R' and the other residues are as defined above.

A further embodiment of the invention is the DHODH inhibitor compound of general formula I, wherein Y is phenyl optionally substituted by R' and the other residues are as defined above.

A further embodiment of the invention is the DHODH inhibitor compound selected from the following list:

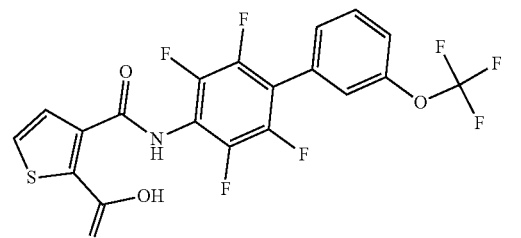

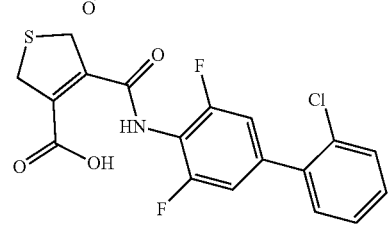

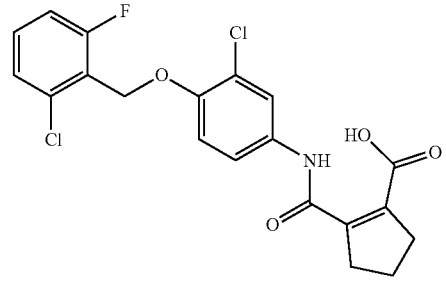

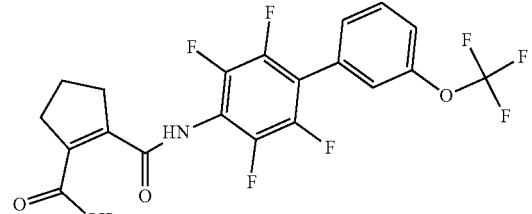

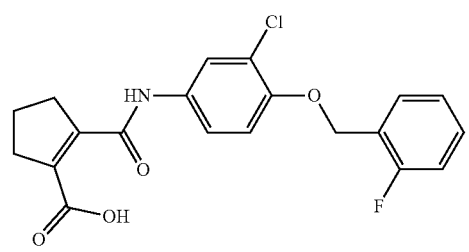

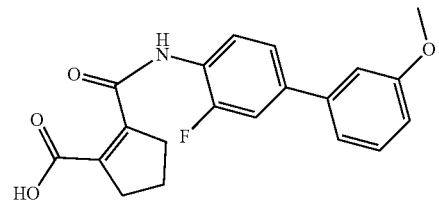

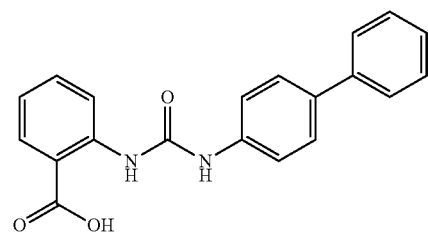

7
-continued
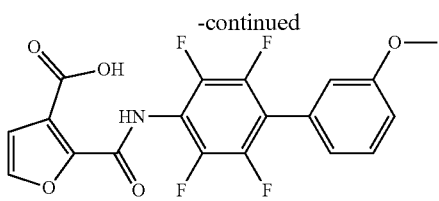
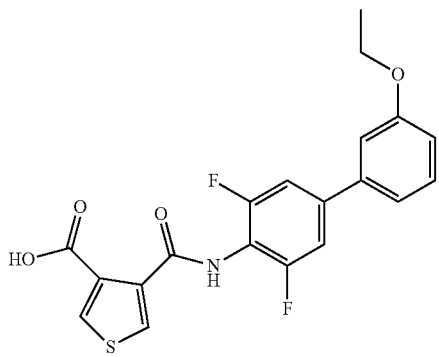
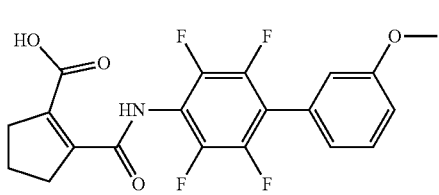
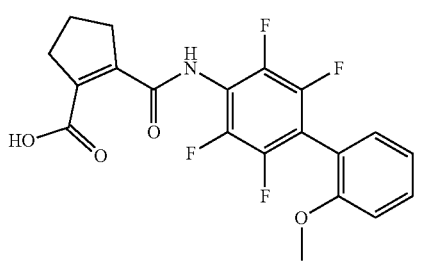
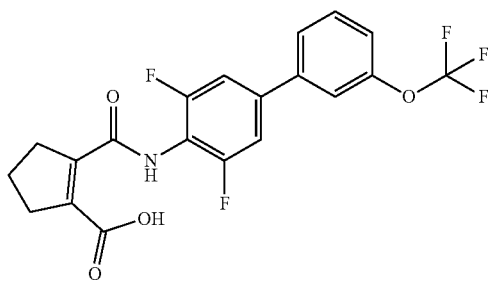
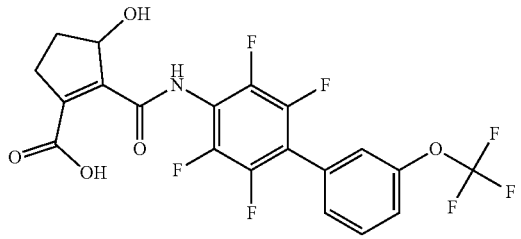
8
-continued
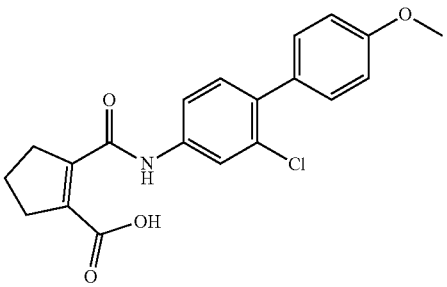
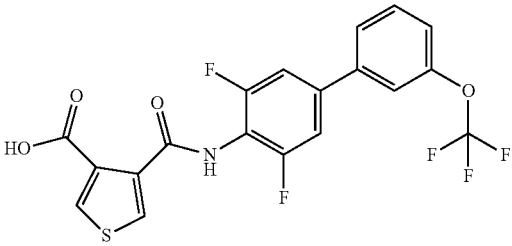
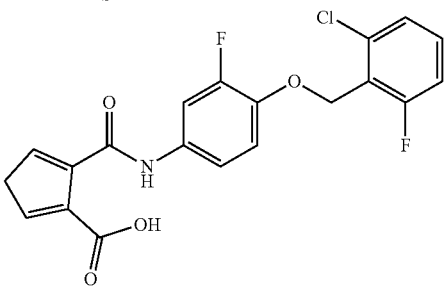
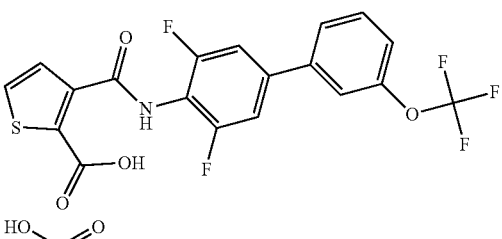
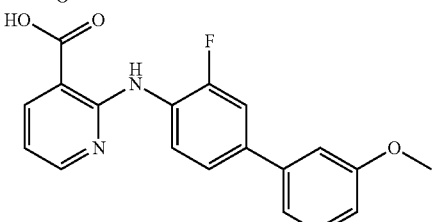
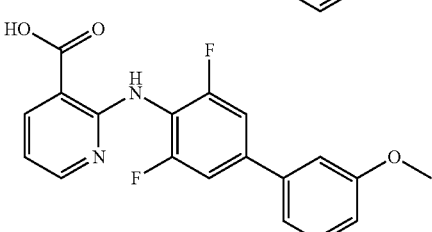
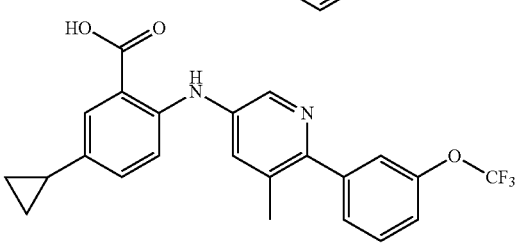

-continued

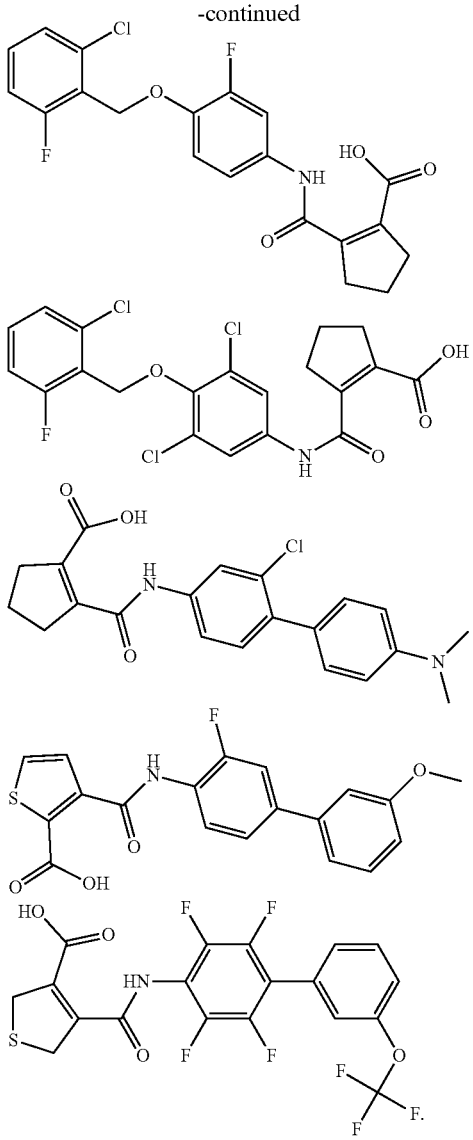

A further embodiment according to the invention is the DHODH inhibitor compound for use as described above, wherein the compound is

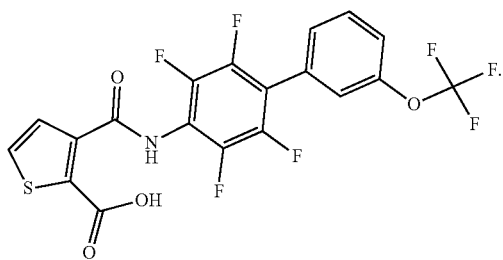
(PP-001)

PP-001 (3-(2,3,5,6-tetrafluoro-3'-trifluoromethoxy-biphenyl-4-ylcarbamoyl)-thiophene-2-carboxylic acid) possesses pronounced antiviral activity.

Leflunomide (5-methyl-N-[4-(trifluoromethyl) phenyl]-isoxazole-4-carboxamide) is an immunosuppressive disease-modifying anti-rheumatic drug (DMARD) used in active moderate to severe rheumatoid arthritis and psoriatic arthritis.

Teriflunomide ((2Z)-2-cyano-3-hydroxy-N-[4-(trifluoromethyl)phenyl]but-2-enamide) is the active metabolite of leflunomide, a disease-modifying agent used in the treatment of multiple sclerosis (MS).

Brequinar (6-fluoro-2-(2'-fluoro-1,1'-biphenyl-4-yl)-3-methyl-4-quinoline-carboxylic acid sodium salt) was originally developed as an anti-proliferative agent for the treatment of cancer.

Vidofludimus (2-(3-fluoro-3'-methoxybiphenyl-4-ylcarbamoyl)-cyclopent-1-enecarboxylic acid has been shown to be active in rodent models of arthritis, multiple sclerosis, psoriasis, and systemic lupus erythematosus. It has been shown to be active in clinical phase two studies to treat rheumatoid arthritis (RA) and inflammatory bowel disease (IBD).

Additional DHODH inhibitors are described, for example, in WO2004056747, WO2004056797, WO2009021696 and WO2011138665.

Unless specified otherwise, the term alkyl, when used alone or in combination with other groups or atoms, refers to a saturated straight or branched chain consisting solely of 1 to 6 hydrogen-substituted carbon atoms, and includes methyl, ethyl, propyl, isopropyl, n-butyl, 1-methylpropyl, isobutyl, t-butyl, 2,2-dimethylbutyl, n-pentyl, 2-methylpentyl, 3-methylpentyl, 4-methylpentyl, n-hexyl and the like.

Unless specified otherwise, the term alkenyl refers to a partially unsaturated straight or branched chain consisting solely of 2 to 6 hydrogen-substituted carbon atoms that contains at least one double bond, and includes vinyl, allyl, 2-methylprop-1-enyl, but-1-enyl, but-2-enyl, but-3-enyl, buta-1,3-dienyl, penta-1,3-dienyl, penta-2,4-dienyl, 2-methylbut-1-enyl, 2-nnethylpent-1-enyl, 4-methylpent-1-enyl, 4-methylpent-2-enyl, 2-methylpent-2-enyl, 4-methylpenta-1,3-dienyl, hexen-1-yl and the like.

Unless specified otherwise, the term alkynyl refers to a partially unsaturated straight or branched chain consisting solely of 2 to 8 hydrogen-substituted carbon atoms that contains at least one triple bond, and includes ethynyl, 1-propynyl, 2-propynyl, 2-methylprop-1-ynyl, 1-butynyl, 2-butynyl, 3-butynyl, 1,3-butadiynyl, 3-methylbut-1-ynyl, 4-methylbut-ynyl, 4-methylbut-2-ynyl, 2-methylbut-1-ynyl, 1-pentynyl, 2-pentynyl, 3-pentynyl, 4-pentynyl, 1,3-pentadiynyl, 1,4-pentadiynyl, 3-methylpent-1-ynyl, 4-methylpent-2-ynyl, 4-methylpent-2-ynyl, 1-hexynyl, and the like.

Unless specified otherwise, the term cycloalkyl, when used alone or in combination with other groups or atoms, refers to a saturated or unsaturated ring consisting solely of 3 to 8 carbon atoms, that may optionally be substituted with one or more, identical or different substituents, suitably one to three substituents, independently selected from $C_{1-4}$alkyl, fluoro-substituted $C_{1-4}$alkyl, halo, $OC_{1-4}$alkyl, fluoro-substituted $OC_{1-4}$alkyl, $NH_2$, NH(alkyl), N(alkyl)$_2$, $CO_2H$, $CO_2$(alkyl), $NO_2$ and CN.

Examples of cycloalkyl groups include cyclopropyl, cyclobutyl, cyclopentyl, cyclohexyl, cycloheptyl, cyclooctyl, cyclopropenyl, cyclobutenyl, cyclopentenyl, cyclohexenyl, cycloheptenyl, cyclooctenyl and the like.

A heterocycloalkyl group denotes a monocyclic non-aromatic hydrocarbon ring containing three to eight carbon atoms, preferably four to eight carbon atoms, or a bicyclic non-aromatic hydrocarbon ring system containing seven to ten carbon atoms, preferably eight to ten carbon atoms, wherein in the heterocycloalkyl group one or more of the carbon atoms of the in the hydrocarbon ring or ring system is replaced by a group selected from the group —N(R$^a$)—, —O—, —S—, —S(O)—, —S(O)$_2$—; wherein the heterocycloalkyl group optionally comprises one or more double bonds, and wherein the heterocycloalkyl group is optionally substituted by one or more residues R' as defined above, and wherein in the heterocycloalkyl group one or two methylene groups may be replaced by a C=O or C=NR$^a$ group.

Non-limiting examples of the heterocycloalkyl group are azepan-1-yl, piperidinyl, in particular piperidin-1-yl and piperidin-4-yl, piperazinyl, in particular N-piperazinyl and 1-alkylpiperazine-4-yl, morpholine-4-yl, tetrahydrofuranyl, tetrahydrothienyl, pyrrolidinyl, tetrahydropyranyl, tetrahydrothiophen, sulfolanyl, sulfolenyl, oxazolinyl, isoxazolinyl, oxazolidinyl, oxazolidinon-yl, wherein in the aforementioned groups optionally one or more of the hydrogen atoms is replaced by a residue R$^a$ as defined above.

Unless specified otherwise, the term aryl refers to an aromatic mono- or bicyclic group containing from 6 to 14 carbon atoms that may be optionally fused with a fully or partially saturated or unsaturated carbocyclic ring and may optionally be substituted with one or more, identical or different substituents, suitably one to three substituents, independently selected from $C_{1-4}$alkyl, fluoro-substituted $C_{1-4}$alkyl, halo, —$OC_{1-4}$alkyl, fluoro-substituted $OC_{1-4}$alkyl, $NH_2$, NH(alkyl), N(alkyl)$_2$, $CO_2H$, $CO_2$(alkyl), $NO_2$ and CN.

Examples of aryl groups include phenyl, naphthyl, indanyl, and the like.

Unless specified otherwise, the term heteroaryl refers to an aromatic mono- or bicyclic group containing from 5 to 14 carbon atoms, of which one to five is replaced with a heteroatom selected from N, S and O, that may optionally be reduced to a nonaromatic heterocycle and may optionally be substituted with one or more, identical or different substituents, suitably one to three substituents, independently selected from $C_{1-4}$alkyl, fluoro-substituted $C_{1-4}$alkyl, halo, $OC_{1-4}$alkyl, fluoro-substituted $OC_{1-4}$alkyl, $NH_2$, NH(alkyl), N(alkyl)$_2$, $CO_2H$, $CO_2$(alkyl), $NO_2$ and CN.

Examples of heteroaryl groups include pyrrolyl, dihydropyrrolyl, pyrrolidinyl, indolyl, isoindolyl, indolizinyl, imidazolyl, pyrazolyl, benzimidazolyl, imidazo(1,2-a)pyridinyl, indazolyl, purinyl, pyrrolo(2,3-c)pyridinyl, pyrrolo(3,2-c)pyridinyl, pyrrolo(2,3-b)pyridinyl, pyrazolo(1,5-a)pyridinyl, 1,2,3-triazolyl, 1,2,4-triazolyl, tetrazolyl, oxazolyl, isoxazolyl, 1,3,4-oxadiazolyl, 1,2,5-oxadiazolyl, 1,2,4-oxadiazolyl, 1,2,3-oxadiazolyl, thiazolyl, isothiazolyl, 1,3,4-thiadiazolyl, 1,2,5-thiadiazolyl, 1,2,4-thiadiazolyl, 1,2,3-thiadiazolyl, furanyl, dihydrofuranyl, tetrahydrofuranyl, benzofuranyl, isobenzofuranyl, thiophenyl, dihydrothiophenyl, tetrahydrothiophenyl, benzothiophenyl, benzoisothiophenyl, pyridyl, piperidinyl, quinolinyl, isoquinolinyl, quinolizinyl, pyrazinyl, pyridazinyl, pyrimidinyl, pyranyl, tetrahydropyranyl, 1,2,3-triazinyl, 1,2,4-triazinyl, 1,3,5-triazinyl, chromenyl, morpholinyl, diazepinyl, benzodiazepinyl, and the like.

A halogen residue is chlorine, bromine, fluorine or iodine, fluorine being preferred.

Ocular diseases are for example, uveitis, optic neuritis, retrobulbar neuritis, ocular inflammation or discomfort or trauma caused by or associated with the use of contact lenses, ocular inflammation, dry eye syndrome, discomfort or trauma caused by or associated with refractive surgery, such as for example radial keratotomy or astigmatic keratotomy, macular degeneration, blepharitis, an optic nerve disease or disorder, such as for example papilledema or a conjunctivitis condition, such as for example allergic conjunctivitis, pink eye, giant papillary conjunctivitis, infectious conjunctivitis or chemical conjunctivitis.

Uveitis is an inflammatory and chronic disease of the eye affecting the uvea, the middle, pigmented layer of the eye. The uvea comprises three parts: the iris (responsible for color), the ciliary body (positioned behind the iris and responsible for lubrication of the eye) and the choroid (vascular lining tissue below the retina). Apart from corticosteroids and immunosuppressives no treatment for such diseases is currently available. Both classes of drugs are known to cause serious side effects when used for a prolonged time period, needed to treat chronic uveitis. Such side effects include osteoporosis, extreme weight gain, diabetes etc. Autoimmune uveitis is associated with immunological response by T helper cells (Th1 and Th17) to human retinal or cross-reactive proteins. These autoreactive T helper cells migrate and infiltrate the eye and are the main cause of the inflammation of the eye. It has been shown in animal models and in humans that neutralizing these deregulated T cells (hallmark cytokines: IFN-γ for Th1 and IL-17 for Th17) lead to an amelioration of clinical uveitis.

Some known DHODH inhibitors are already used to treat inflammatory diseases, e.g. Arava® to treat rheumatoid arthritis or Aubagio® to treat multiple sclerosis. However, such medications are provided as tablets or intravenous injections and gain therapeutic activity by having a systemic effect on the whole body. Fang C B et al. (2013) have also been shown previously that systemic administration of the DHODH inhibitor Leflunomide is useful to treat experimental autoimmune uveitis in a rat model. However, due to the ocular-blood-barrier, very high systemic blood levels of Leflunomide are necessary to reach therapeutically efficient drug levels in the eye. Such high blood levels of an immunosuppressive drug may result in inadequate systemic side effects when treating an eye disease.

It was surprisingly found by the inventors that DHODH inhibitor compounds are highly efficacious and well tolerated when used to treat eye diseases by local administration to the eye.

Thus, a further embodiment of the invention relates to the DHODH inhibitor compound for use in the treatment of uveitis.

The most common form of conjunctivitis is caused by adenoviral infection. This type of conjunctivitis may also spread to affect the cornea (keratitis), and may persist for several weeks and cause hazy vision. Since the disease is often epidemic in nature, it is called epidemic keratoconjunctivitis—EKC is a serious and contagious form of conjunctivitis (conjunctiva and cornea). A recent outbreak of adenoviral conjunctivitis in northern Germany in December 2012 was a major topic in the daily news. The majority of cases of EKC are believed to be caused by a select species of adenoviruses, including Ad8, Ad19 and Ad37.

Thus, a further embodiment of the invention relates to the DHODH inhibitor compound for use in the treatment of conjunctivitis.

Adenoviruses are known to cause upper and lower respiratory tract infections, several varieties of viral conjunctivitis (including keratoconjunctivitis), as well as gastroenteritis and hemorrhagic cysts, though only certain serotypes are associated with each. With regard to ocular infections, adenoviruses present a serious public health risk and are responsible for 65 to 90% of viral conjunctivitis and 15 to 70% of all cases of infectious conjunctivitis worldwide.

Thus, a further embodiment of the invention relates to the DHODH inhibitor compound for use in the treatment of an ocular disease caused by an adenovirus.

Keratoconjunctivitis sicca (KCS), also called keratitis sicca, xerophthalmia or dry eye syndrome (DES) is an eye disease caused by eye dryness, which, in turn, is caused by either decreased tear production or increased tear film evaporation. It is found in humans and some animals. KCS is the most common eye disease, affecting 5-6% of the population.

Thus, a further embodiment of the invention relates to the DHODH inhibitor compound for use in the treatment of dry eye syndrome.

Age-related macular degeneration (AMD) is a medical condition that usually affects older adults and results in a loss of vision in the center of the visual field (the macula) because of damage to the retina. It occurs in "dry" and "wet" forms. It is a major cause of blindness and visual impairment in older adults (>50 years). In the wet form (wet AMD), which is more severe, blood vessels grow up from the choroid behind the retina, and the retina can become detached. Wet AMD has a prevalence of around 1.5% among the population.

Thus, a further embodiment of the invention relates to the DHODH inhibitor compound for use in the treatment of wet age-related macular degeneration.

A further embodiment of the invention relates to a DHODH inhibitor compound which is administered to a subject in a therapeutically effective amount.

As used herein, the term "subject" can be any singular or plural subject, including, but not limited to humans and animals, e.g. mammals or birds, specifically from horses, poultry, pigs, cattle, rodents and pets. Said subjects can be healthy subjects or any subjects suffering or going to suffer from an ocular disease.

As used herein, the terms "therapeutically effective amount" or "effective amount" refer to the amount of drug required to confer a biological or meaningful subject benefit, such as the biological or medical response or improvement sought by a medical doctor or other medical professional. In one aspect, the terms "therapeutically effective amount" or "effective amount" are intended to mean the amount of drug that will bring about a biologically meaningful improvement in the subject's ocular disorder, symptom, or disease. Doses that exhibit large therapeutic indices are preferred. Effective amounts may vary, as recognized by those skilled in the art, depending, for example, on route of administration, dosage form, inclusion of additional active agents, as well as age, weight, sensitivity, and health of the subject.

The treatment regimen for the ocular disease can vary depending on the particular needs of the subject. For example, the dose and frequency of administration of the DHODH inhibitor compound may depend in part on the age of the subject and severity of ocular disease and the route of administration. By way of non-limiting illustration, the DHODH inhibitor may be applied topically (e.g. in form of eye drops) between once daily and up to eight times a day. Some patients may benefit from regular application of the formulation, such as for at least for about 3 days, in another aspect at least for about 10 days, in a further aspect for at least about 1 month and yet in another aspect at least for about 3 months. A shorter or longer treatment regimen may be used, if desired.

By way of non-limiting illustration, the DHODH inhibitor may also be applied into the eye, e.g. as intravitreal injection or implant. In contrast to topical eye drops, injections are applied significantly less frequent.

Diseases of posterior segments of the eye are often intractable, and a development of an effective pharmacotherapy is eagerly desired. However, the drugs are hardly delivered to the posterior segments of the eye. Even if the drugs are delivered to the posterior segments of the eye, it is very difficult to maintain a drug concentration in those tissues.

Intravenous injection, oral administration or a intravitreous injection are attempted to administer the drugs for the diseases of the posterior segments of the eye. However, the intravenous injection and the oral administration can deliver only a very small amount of drugs to the posterior segments of the eye which are target sites, and sometimes causes unexpected strong systemic actions (side effects) of the drugs.

In the case of the intravitreous injection, since the drug is directly injected into the eye, the amount of the drug to be delivered to the posterior segments of the eye is larger than those of the intravenous injection and the oral administration.

Ideally, a formulation for intravitreal injections releases the drug continuously over a longer period of time at a release rate which ensures continuous therapeutic concentration at the desired site of action of the DHODH inhibitor. Examples for such formulations are PLGA nano-spheres or PLGA microspheres. In such formulations, the DHODH inhibitor is embedded in small spheres of PLGA polymers and slowly released within the eye while the PLGA is degraded. Depending on the ratio of lactic acid and glycolic acid and the degree of crosslinking of the polymer and depending on the manufacturing process of the spheres, complete drug can be released within 1 week to 1 month, preferred within 6 months, and more preferred within 12 months or longer periods. A slow release of therapeutically active amounts of the DHODH inhibitor from the formulation after intravitreal injection aims to reduce the intervals between single injections into the eye. Similar results can be obtained with implants.

The active ingredient of the invention (e.g. DHODH inhibitor compound) may be combined with pharmaceutically acceptable excipients, and optionally sustained-release matrices, such as biodegradable polymers, to form a pharmaceutical composition.

The active ingredient of the invention may be administered locally to the eyes of the subjects to be treated for avoiding the potential negative side effects of the administration in the systemic circulation.

Accordingly, the pharmaceutical composition of the invention is formulated for a local ocular route administration such as intravitreous, topical, periocular injections (subconjunctival, peribulbar, laterobulbar, retrobulbar, subtenon, suprachoroidal), intra- or periocular implants (intrascleral, periscleral, episcleral), intravitreous implants or suprachoroidal implants or particles or polymeric composition, or any releasing systems such as emulsions, solid non-biodegradable or degradable implants or tablets, mini pumps or any topical formulations.

Preferably, the pharmaceutical composition contains vehicles which are pharmaceutically acceptable for a formulation capable of being injected into the eye. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical compositions suitable for injectable use in the eye include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and may be preserved against the contaminating action of microorganisms, such as bacteria, virus and fungi.

Solutions comprising a DHODH inhibitor compound of the invention as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations may contain a preservative to prevent the growth of microorganisms.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, benzalkonium chloride, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions for the eyes are prepared by incorporating the active ingredients of the invention in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as it is therapeutically effective. The formulations are easily administered in a variety of dosage forms, such as the type of injectable solutions described above, but drug release capsules and the like may also be employed.

The active ingredient may be also delivered directly to the eye by ocular tissue injection such as periocular, conjunctival, subtenon, intracameral, intravitreal, intraocular, subretinal, subconjunctival, retrobulbar, suprachoroidal or intracanalicular injections; by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or in the sclera (intrascleral) or suprachoroidal or within the eye. Intracameral injection may be through the cornea into the anterior chamber to allow the agent to reach the trabecular meshwork. Intracanalicular injection may be into the venous collector channels draining Schlemm's canal or into Schlemm's canal.

For ophthalmic delivery, the active ingredient may be combined with ophthalmologically acceptable preservatives, co-solvents, surfactants, viscosity enhancers, penetration enhancers, buffers, sodium chloride, or water to form an aqueous, sterile ophthalmic suspension or solution. Solution formulations may be prepared by dissolving the active ingredient in a physiologically acceptable isotonic aqueous buffer. Further, the solution may include an acceptable surfactant to assist in dissolving the active ingredient. Viscosity building agents, such as hydroxymethyl cellulose, hydroxyethyl cellulose, hydroxypropyl methylcellulose, methylcellulose, carboxymethylcellulose, polyvinylpyrrolidone, hyaluronic acid, or the like may be added to the compositions of the present invention to improve the retention of the compound.

In order to prepare a sterile ophthalmic ointment formulation, the active ingredient is combined with a preservative in an appropriate vehicle, such as mineral oil, liquid lanolin, or white petrolatum. Sterile ophthalmic gel formulations may be prepared by suspending the active ingredient in a hydrophilic base prepared from the combination of, for example, CARBOPOLO-940 (BF Goodrich, Charlotte, NC), or the like, according to methods known in the art. VISCOATCD (Alcon Laboratories, Inc., Fort Worth, TX) may be used for intraocular injection, for example. Other compositions of the present invention may contain penetration enhancing agents such as cremophor and TWEENCD 80 (polyoxyethylene sorbitan monolaureate, Sigma Aldrich, St. Louis, MO), in the event the active ingredient is less penetrating in the eye.

In a particular embodiment, the pharmaceutical composition of the invention is an ophthalmic drop formulation. The eye drop is provided in any formulation generally used, for example, in the form of an aqueous eye drop such as aqueous eye drop solution, aqueous eye drop suspension, viscous eye drop solution, solubilized eye drop solution and the like, or in the form of a non-aqueous eye drop such as a non-aqueous eye drop solution, non-aqueous eye drop suspension and the like. When the composition of the present invention is prepared as an aqueous eye drop, it preferably contains an additive which is usually used in an aqueous eye drop. The examples of such an additive include preservatives, isotonic agents, buffering agents, stabilizer, pH regulators or the like.

In another particular embodiment, the active ingredients of the invention are delivered through a biodegradable ocular implant.

The implants can be formed in a manner that the active ingredient is homogenously distributed or dispersed throughout the biodegradable polymer matrix. Additionally, the implants can be formed to release the active ingredient into an ocular region of the eye over various time periods. Thus, the active ingredient can be released from implants made according to the present invention for a period of time of, for example, 30-200 days.

The active ingredient can comprise from about 10% to about 90% by weight of the implant. In one variation, the agent is from about 40% to about 80% by weight of the implant. In a preferred variation, the agent comprises about 60% by weight of the implant.

In a particular embodiment, the active ingredient can be homogeneously dispersed in the biodegradable polymer of the implant. The implant can be made, for example, by a sequential or double extrusion method. The selection of the biodegradable polymer used can vary with the desired release kinetics, subject tolerance, the nature of the disease to be treated, and the like. Polymer characteristics that are considered include, but are not limited to, the biocompatibility and biodegradability at the site of implantation, compatibility with the active ingredient of interest, and processing temperatures. The biodegradable polymer matrix usually comprises at least about 10, at least about 20, at least about 30, at least about 40, at least about 50, at least about 60, at least about 70, at least about 80, or at least about 90 weight percent of the implant. In one variation, the biodegradable polymer matrix comprises about 40% to 50% by weight of the implant.

Biodegradable polymers which can be used include, but are not limited to, polymers made of monomers such as organic esters or ethers, which when degraded result in physiologically acceptable degradation products. Anhydrides, amides, orthoesters, or the like, by themselves or in combination with other monomers, may also be used. The polymers are generally condensation polymers. The polymers can be crosslinked or non-crosslinked. If crosslinked, they are usually not more than lightly crosslinked, and are less than 5% crosslinked, usually less than 1% crosslinked. Of particular interest are polymers of hydroxyaliphatic carboxylic acids, either homo- or copolymers, and polysaccharides. Included among the polyesters of interest are homo- or copolymers of D-lactic acid, L-lactic acid, racemic lactic acid, glycolic acid, caprolactone, and combinations thereof. Copolymers of glycolic and lactic acid are of particular interest, where the rate of biodegradation is controlled by the ratio of glycolic to lactic acid. The percent of each monomer in poly(lactic-co-glycolic)acid (PLGA) copolymer may be 0-100%, about 15-85%, about 25-75%, or about 35-65%. In certain variations, 25/75 PLGA and/or 50/50 PLGA copolymers are used. In other variations, PLGA copolymers are used in conjunction with polylactide polymers or polyurethanes.

Other agents may be employed in the formulation for a variety of purposes. For example, buffering agents and preservatives may be employed. Preservatives which may be used include, but are not limited to, sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. Examples of buffering agents that may be employed include, but are not limited to, sodium carbonate, sodium borate, sodium phosphate, sodium acetate, sodium bicarbonate, and the like, as approved by the FDA for the desired route of administration. Electrolytes such as sodium chloride and potassium chloride may also be included in the formulation.

The formulation according to the invention may further comprise an anti-phlogistic or antibiotic agent like azithromycin, specifically an agent with additional anti-inflammatory properties, specifically histamine antagonists or non-steroidal anti-inflammatory drugs.

The formulation of the invention may also be formulated as depot formulation which provides continuous or prolonged administration.

According to a further embodiment of the invention, the formulation can be used in preventing recurrence of ocular infections in a subject.

According to a further embodiment of the invention, the formulation can be used in preventing recurrence of ocular inflammations in a subject.

Preferably, the formulations of the present invention are stable in a wide range of temperatures.

The invention also provides that the formulation be packaged in a hermetically sealed container such as an ampoule or sachette indicating the quantity of formulation.

In one embodiment, the formulation is supplied as a liquid, in another embodiment, as a dry sterilized lyophilized powder or water free concentrate, or as dry and sterile nano- or microspheres of drug-containing PLGA copolymers in a hermetically sealed container and can be reconstituted, e.g., with water or saline to the appropriate concentration for administration to a subject.

In an alternative embodiment, the composition is supplied in liquid form in a hermetically sealed container indicating the quantity and concentration of the composition.

The invention furthermore comprises the following items:
1. A DHODH inhibitor compound for use in local drug delivery in a method to treat an ocular disease.
2. The compound for use according to item 1, wherein the compound is selected from the group consisting of leflunomide, teriflunomide, vidofludimus, brequinar, ASLAN003 or a compound of general formula I,

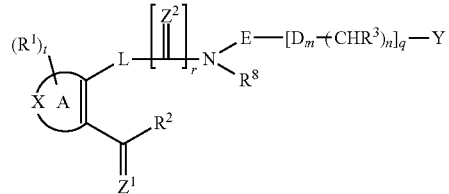

wherein
A is an aromatic or non-aromatic 5- or 6-membered hydrocarbon ring wherein optionally one or more of the carbon atoms are replaced by a group X, wherein X is independently selected from the group consisting of S, O, N, $NR^4$, $SO_2$ and SO;
L is a single bond or NH;
D is O, S, $SO_2$, $NR^4$, or $CH_2$;
$Z^1$ is O, S, or $NR^5$;
$Z^2$ is O, S, or $NR^5$;
$R^1$ independently represents H, halogen, haloalkanyl, haloalkenyl, haloalkynyl, haloalkanyloxy, haloalkenyloxy, haloalkynyloxy, —$CO_2R''$, —$SO_3H$, —OH, —CONR*R'', —CR''O, —$SO_2$—NR*R'', —$NO_2$, —$SO_2$—R'', —SO—R*, —CN, alkanyloxy, alkenyloxy, alkynyloxy, alkenylthio, alkenylthio, alkynylthio, aryl, —NR''—$CO_2$—R', —NR''—CO—R*, —NR''—$SO_2$—R', —O—CO—R*, —O—$CO_2$—R*, —O—CO—NR*R'', cycloalkyl, heterocycloalkyl, alkenylamino, alkenylamino, alkynylamino, hydroxyalkanylamino, hydroxyalkenyl-amino, hydroxyalkynylarnino, —SH, heteroaryl, alkanyl, alkenyl or alkynyl;
R* independently represents H, alkanyl, alkenyl, alkynyl, cycloalkyl, heterocyclo-alkyl, aminoalkanyl, aminoalkenyl, aminoalkynyl, alkanyloxy, alkenyloxy, alkynyloxy, —OH, —SH, alkanylthio, alkenylthio, alkynylthio, hydroxyalkanyl, hydroxyalkenyl, hydroxyalkynyl, haloalkanyl, haloalkenyl, haloalkynyl, haloalkanyloxy, haloalkenyloxy, haloalkynyloxy, aryl or heteroaryl;
R' independently represents H, —$CO_2R''$, —CONR''R''', —CR''O, —$SO_2NR''$, —NR''—CO-haloalkanyl, haloalkenyl, haloalkynyl, —$NO_2$, —NR''—$SO_2$-haloalkanyl, haloalkenyl, haloalkynyl, —NR''—$SO_2$-alkanyl, —NR''—$SO_2$-alkenyl, —NR''—$SO_2$-alkynyl, —SO₂-alkanyl, —SO₂-alkenyl, —SO₂-alkynyl, —NR''—CO-alkanyl, —NR''—CO-alkenyl, —NR''—CO-alkynyl, —CN, alkanyl, alkenyl, alkynyl, cycloalkyl, heterocycloalkyl, aminoalkanyl, aminoalkenyl, aminoalkynyl, alkanylamino, alkenylamino, alkynylamino, alkanyloxy, alkenyloxy, alkynyloxy, cycloalkyloxy, —OH, —SH, alkanylthio, alkenylthio, alkynylthio, hydroxyalkanyl, hydroxyalkenyl, hydroxyalkynyl, hydroxyalkanylamino, hydroxyalkenyl-amino, hydroxyalkynylamino, halogen, haloalkanyl, haloalkenyl, haloalkynyl, haloalkanyloxy, haloalkenyloxy, haloalkynyloxy, aryl, aralkyl or heteroaryl;

R'' independently represents hydrogen, haloalkanyl, haloalkenyl, haloalkynyl, hydroxyalkanyl, hydroxyalkenyl, hydroxyalkynyl, alkanyl, alkenyl, alkynyl, cycloalkyl, heterocycloalkyl, aryl, heteroaryl, aminoalkanyl, aminoalkenyl or aminoalkynyl;

R''' independently represents H or alkanyl;

$R^2$ is H or $OR^6$, $NHR^7$, $NR^7OR^7$;

or $R^2$ together with the nitrogen atom which is attached to $R^8$ forms a 5 to 7 membered, preferably 5 or 6 membered heteroyclic ring wherein $R^2$ is —[CH₂]$_s$ and $R^8$ is absent;

$R^3$ is H, alkanyl, alkenyl, alkynyl, cycloalkyl, heterocycloalkyl, aryl, alkanyloxy, alkenyloxy, alkynyloxy, —O-aryl; —O-cycloalkyl, —O-heterocycloalkyl, halogen, amino-alkanyl, aminoalkenyl, aminoalkynyl, alkanylamino, alkenylamino, alkynylamino, hydroxylamino, hydroxylalkanyl, hydroxylalkenyl, hydroxylalkynyl, haloalkanyloxy, haloalkenyloxy, haloalkynyloxy, heteroaryl, alkanylthio, alkenylthio, alkynylthio, —S-aryl; —S-cycloalkyl, —S-heterocycloalkyl, aralkyl, haloalkanyl, haloalkenyl or haloalkynyl;

$R^4$ is H, alkanyl, alkenyl, alkynyl, cycloalkyl, heterocycloalkyl, aryl or heteroaryl;

$R^5$ is H, OH, alkanyloxy, alkenyloxy, alkynyloxy, O-aryl, alkanyl, alkenyl, alkynyl or aryl;

$R^6$ is H, alkanyl, alkenyl, alkynyl, cycloalkyl, heterocycloalkyl, aryl, heteroaryl, aralkyl, alkanyloxyalkanyl, alkanyloxyalkenyl, alkanyloxyalkynyl, alkenyloxyalkanyl, alkenyloxyalkenyl, alkenyloxyalkynyl, alkynyloxyalkanyl, alkynyloxyalkenyl, alkynyloxy-alkynyl, acylalkanyl, (acyloxy)alkanyl, (acyloxy)alkenyl, (acyloxy)alkynyl acyl, non-symmetrical (acyloxy)alkanyldiester, non-symmetrical (acyloxy)alkenyldiester, non-symmetrical (acyloxy)alkynyldiester, or dialkynylphosphate, dialkenylphosphate or dialkynylphosphate;

$R^7$ is H, OH, alkanyl, alkenyl, alkynyl, aryl, alkanyloxy, alkenyloxy, alkynyloxy, —O-aryl, cycloalkyl, heterocycloalkyl, —O-cycloalkyl, or —O-heterocycloalkyl;

$R^8$ is H, alkanyl, alkenyl or alkynyl;

E is an alkanyl, alkenyl, alkynyl, aryl, heteroaryl, heterocycloalkyl or cycloalkyl group or a fused bi- or tricyclic ring system wherein one phenyl ring is fused to one or two monocyclic cycloalkyl or heterocycloalkyl rings or one bicyclic cycloalkyl or heterocycloalkyl ring, or wherein two phenyl rings are fused to a monocyclic cycloalkyl or heterocycloalkyl ring, wherein monocyclic and bicyclic cycloalkyl and heterocyclo-alkyl rings are as defined herein, and wherein all of the aforementioned groups may optionally be substituted by one or more substituents R';

Y is H, halogen, haloalkanyl, haloalkenyl, haloalkynyl, haloalkanyloxy, haloalkenyloxy, haloalkynyloxy, alkanyl, alkenyl, alkynyl, aryl, heteroaryl, heterocycloalkyl or cycloalkyl group or a fused bi- or tricyclic ring system wherein one phenyl ring is fused to one or two monocyclic cycloalkyl or heterocycloalkyl rings or one bicyclic cycloalkyl or heterocycloalkyl ring, or wherein two phenyl rings are fused to a monocyclic cycloalkyl or heterocycloalkyl ring, and wherein all of the aforementioned groups may optionally be substituted by one or more substituents R', or Y is

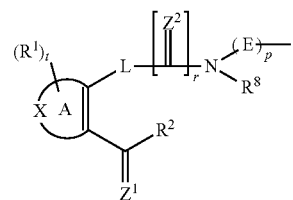

wherein $R^1$, X, A, $Z^1$, $Z^2$, $R^8$, $R^2$, E and p are as defined herein;

m is 0 or 1;
n is 0 or 1;
p is 0 or 1;
q is 0 or 1;
r is 0 or 1;
s is 0 to 2; and
t is 0 to 3.

3. The compound for use according to item 2, wherein the compound is selected from the following list:

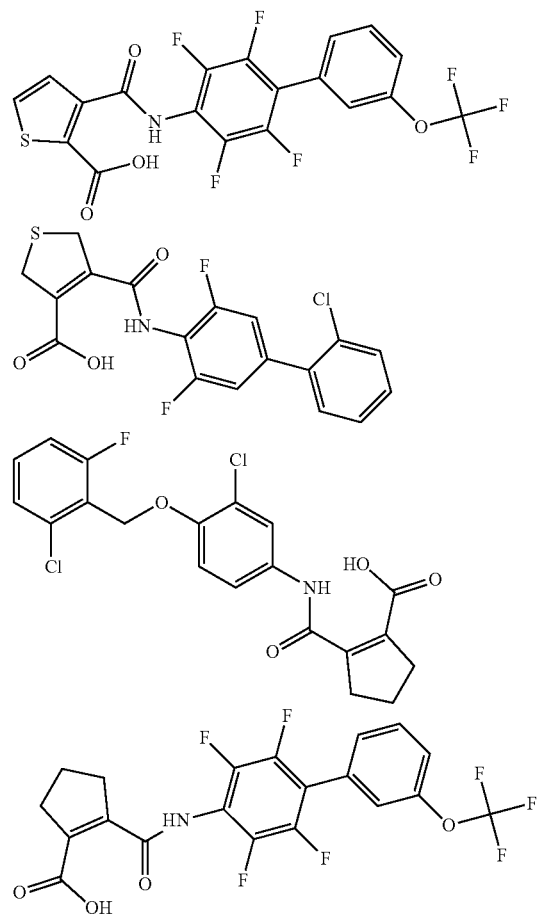

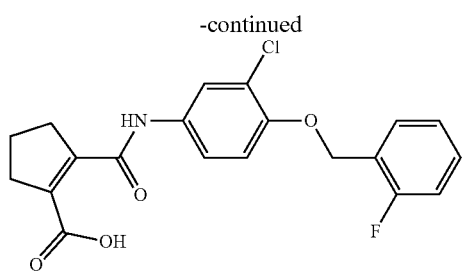
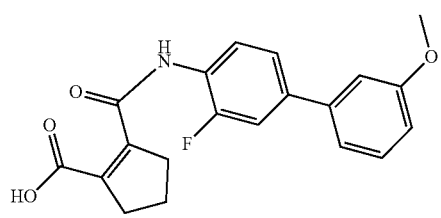
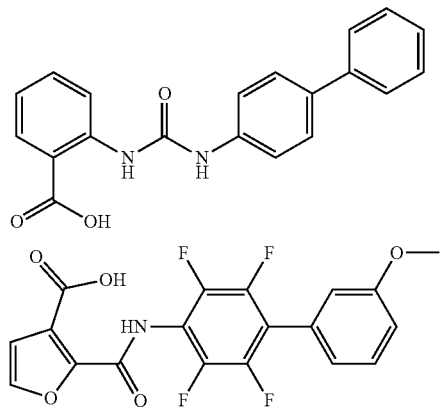
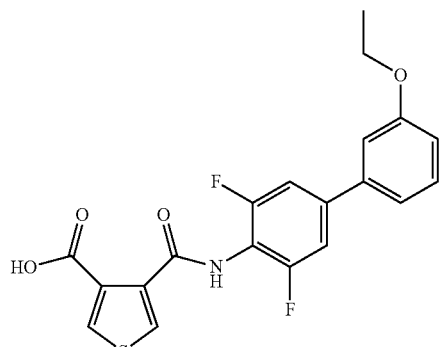
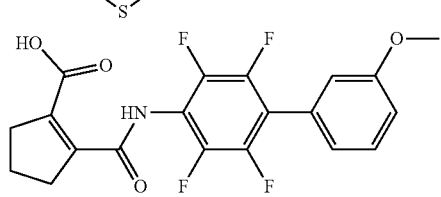
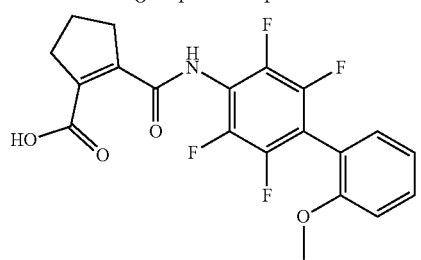
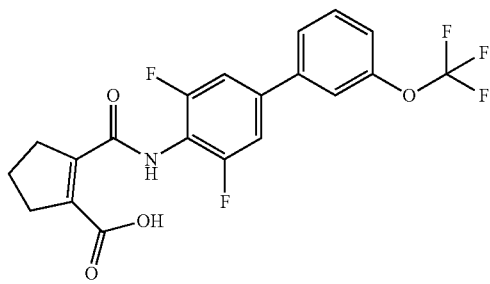
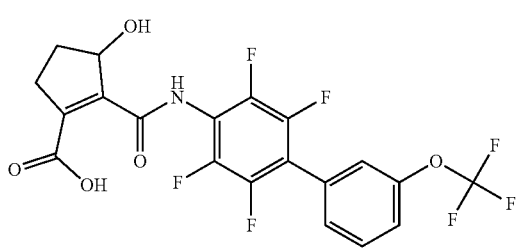
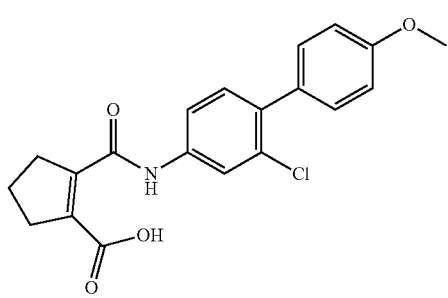
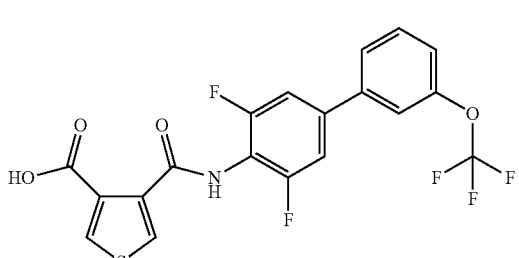
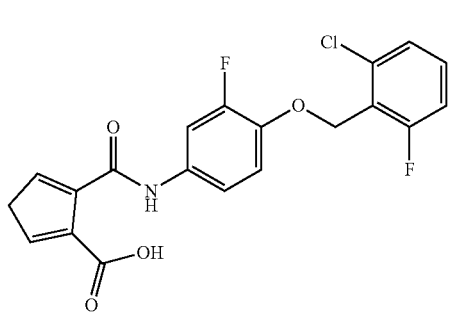
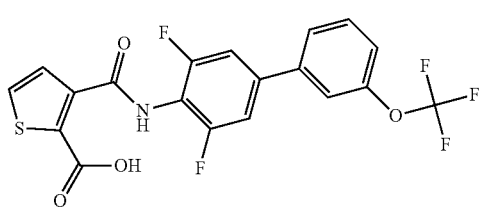

-continued

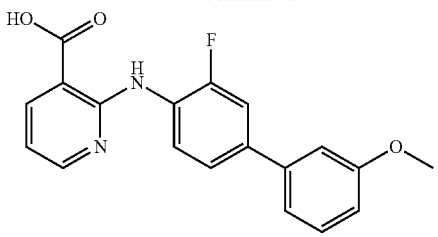
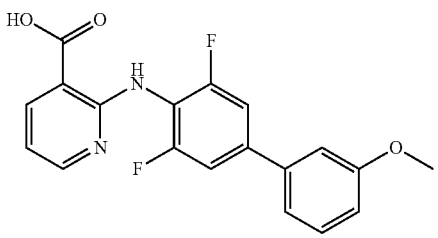
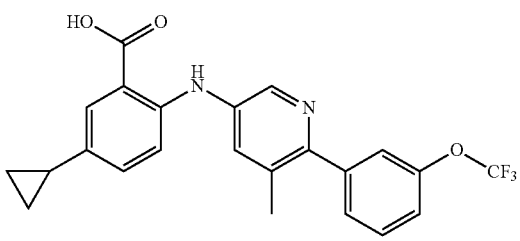
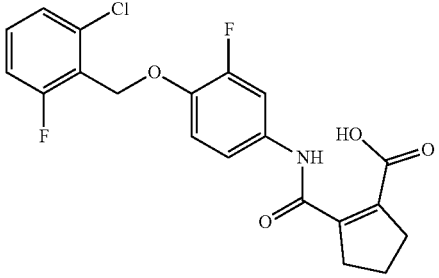
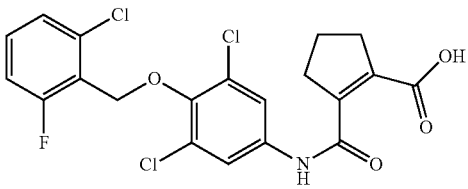
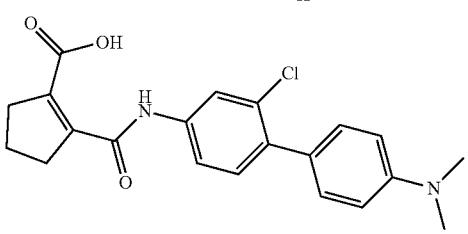
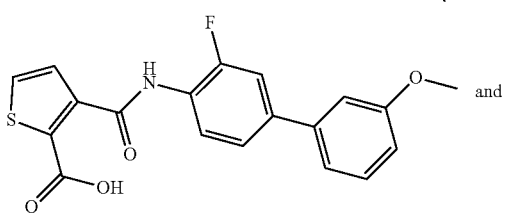

-continued

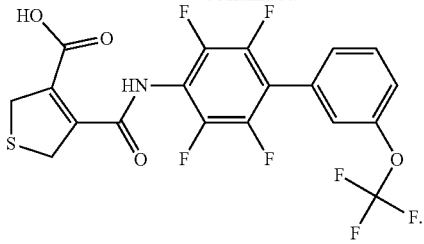

4. The compound for use according to item 3, wherein the compound is

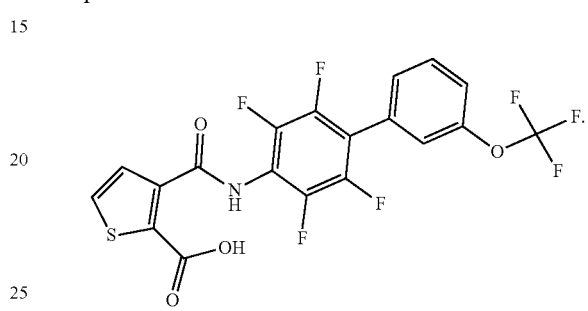

5. The compound for use according to any one of items 1 to 4, wherein the ocular disease is uveitis, optic neuritis, retrobulbar neuritis, ocular inflammation or discomfort or trauma caused by or associated with the use of contact lenses, ocular inflammation, discomfort or trauma caused by or associated with refractive surgery, blepharitis, an optic nerve disease or disorder, or a conjunctivitis condition.

6. The compound for use according to item 5, wherein the subject is suffering from uveitis, dry eye, age-related macular degeneration (AMD), conjunctivitis (pink eye), keratitis, keratoconjunctivitis, vernal keratoconjunctivitis (VKC), or atopic keratoconjunctivitis (AKC).

7. The compound for use according to item 6, wherein the ocular disease is uveitis, dry eye, age-related macular degeneration (AMD) or conjunctivitis.

8. The compound for use according to claim 7, wherein the subject is suffering from age-related macular degeneration (AMD).

9. The compound for use according to any one of items 1 to 4, wherein the ocular disease is caused by an adenovirus.

10. The compound for use according to any one of items 1 to 9, wherein the DHODH inhibitor compound is administered to the subject in a therapeutically effective amount.

11. The compound for use according to any one of items 1 to 10, wherein the compound is administered at least once per day.

12. The compound for use according to any one of items 1 to 10, wherein the compound is administered as a slow release formulation at least once per month, or at least every second month, or at least every third month preferably at least every sixth month.

13. The compound for use according to any one of items 1 to 10 in a method for treating an ocular disease through injection of said compound into the vitreous body with a frequency of injections not exceeding one injection per month.

14. A pharmaceutical composition comprising a therapeutically effective amount of at least one DHODH inhibitor according to any one of items 1 to 4 for use in the treatment of an ocular disease.

15. The pharmaceutical composition according to item 14, comprising the compound according to any one of items 1 to 4, together with a pharmaceutically acceptable excipient therefor.

16. The pharmaceutical composition according to item 15, wherein the excipient is selected from the group of hydrophilic polymer excipients, tonicity agents, buffers, sugars such as trehalose, mannose, D-galactose, and lactose, preservatives, co-solvents or antioxidants.

17. The pharmaceutical composition according to any one of items 14 to 16, which is formulated for a local ocular route administration such as intravitreous, topical, periocular injections (sub conjunctival, peribulbar, laterobulbar, retrobulbar, subtenon, suprachoroidal), intra- or periocular implants (intrascleral, periscleral, episcleral), intravitreous implants or suprachoroidal implants or particles or polymeric composition, or any releasing systems such as emulsions, solid non-biodegradable or degradable implants or tablets, mini pumps or any topical formulations.

18. The pharmaceutical composition according to any one of items 14 to 17, which is a sterile eye drop formulation, a suspension, an emulsion, a microsphere formulation or a sterile solution by intravitreal injection.

19. An ophthalmic formulation of a pharmaceutical composition according to any one of items 14 to 18.

20. The formulation according to item 19 as a sterile eye drop formulation or as a sterile solution for intravitreal injection.

21. The formulation according to item 19 or 20, wherein the frequency of administration is once daily or in the range from about one to about eight times a day, once per week, once per month, every second month or every third month or every sixth month.

22. The formulation according to any one of items 19 to 21, wherein a therapeutically effective amount of the compound reaches the posterior segment of the eye.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

The Examples which follow are set forth to aid in the understanding of the invention but are not intended to, and should not be construed to limit the scope of the invention in any way. The Examples do not include detailed descriptions of conventional methods, e.g., cloning, transfection, and basic aspects of methods for overexpressing proteins in microbial host cells. Such methods are well known to those of ordinary skill in the art.

Example 1: Local Tolerability of Intravitreal Injections of PP-001

Intraocular (=local) application of drugs for uveitis is a desirable way of treatment to avoid systemic treatment, which is often burdened with severe side effects.

For this purpose, three different doses of PP-001, dissolved in phosphate-buffered saline (PBS) and a vehicle control with PBS only were injected into the posterior chamber (=vitreous) of rat eyes. The eyes (anterior chamber) were examined daily with an ophthalmoscope and after 8 days the experiment was terminated, and the eyes processed for histology (cryosections).

8 Lewis rats (age 7-8 weeks) were anesthetized using 0.5 mg/kg medetomidine s.c. Additional topical anesthesia with 0.4% oxybuprocaine eye drops was applied. After intraocular injection sedation was antagonized with an s.c. injection of 2.5 mg/kg atipamezol.

10 µl of solution were injected into the vitreous of both eyes with a 30 G needle, controlled under an operation microscope. The perpendicular injection is penetrating the cornea and should neither touch the lens or the retina. After injection an antibiotic ointment was applied to the eyes to avoid infections.

PP-001 was dissolved in PBS and applied intravitreally in 3 different concentrations.

Group designations:
  Group 1, Rat 1-1 and 1-2: 10 µl PBS (vehicle control)
  Group 2, Rat 2-1 and 2-2: 10 µl PP-001: 1.5 µg/ml
  Group 3, Rat 3-1 and 3-2: 10 µl PP-001: 15 µg/ml
  Group 4, Rat 4-1 and 4-2: 10 µl PP-001: 150 µg/ml All clinically visible abnormalities could be confirmed by histology and were due to the intraocular injection, irrespective of the substance (PBS only or PP-001) or the dose. The histological findings in cornea and retina were only focal and could be assigned to the sites of injection. Since there were no differences between the vehicle-injected group and the groups that had received various doses of PP-001, and since 2 of 4 eyes of the high dose PP-001 were completely normal we would assume that intraocular application of PP-001 has no toxic effect on intraocular tissues. From our primary results of 8 days observation we would conclude that intraocular PP-001 is safe.

Example 2: Prevention of Relapses in the Experimental Autoimmune Uveitis Rat Model by Intravitreal Injection of PP-001

Experimental autoimmune uveitis (EAU) in Lewis rats is a model for human endogenous uveitis. The disease is mediated by CD4+ T lymphocytes of the T helper 1 (Th1) and Th17 subtypes. In Lewis rats the disease was induced by immunizing animals with retinal antigens such as interphotoreceptor retiniod-binding protein (IRBP) and adjuvant. IRBP is also considered to be an autoantigen in humans.

Peptide R14, a 23 mer from IRBP, is the most pathogenic epitope for Lewis rats. Immunization with these peptides emulsified in Complete Freund's Adjuvant (CFA) leads to severe inflammation of the anterior chamber of the eyes and destruction of the retinal architecture.

R14 causes a relapsing-remitting disease with an early onset (about day 7), the peak of EAU between day 10 to 14 and the remission around day 17/18.

20 rats were immunized with 15 µg IRBP-peptide R14 emulsified in complete Freund's adjuvant. After primary disease, PP-001 was injected intravitreally at day 18 (6 µl=3 µg PP-001) in both eyes of 10 animals. One eye in this group dropped out because of penetrating the eye during injection.

10 animals received 6 µl PBS intravitreally in both eyes as control group. Clinical grade of inflammation in the anterior chamber was determined daily.

PP-001 reduced the number of relapses by >50%

Figure 1:
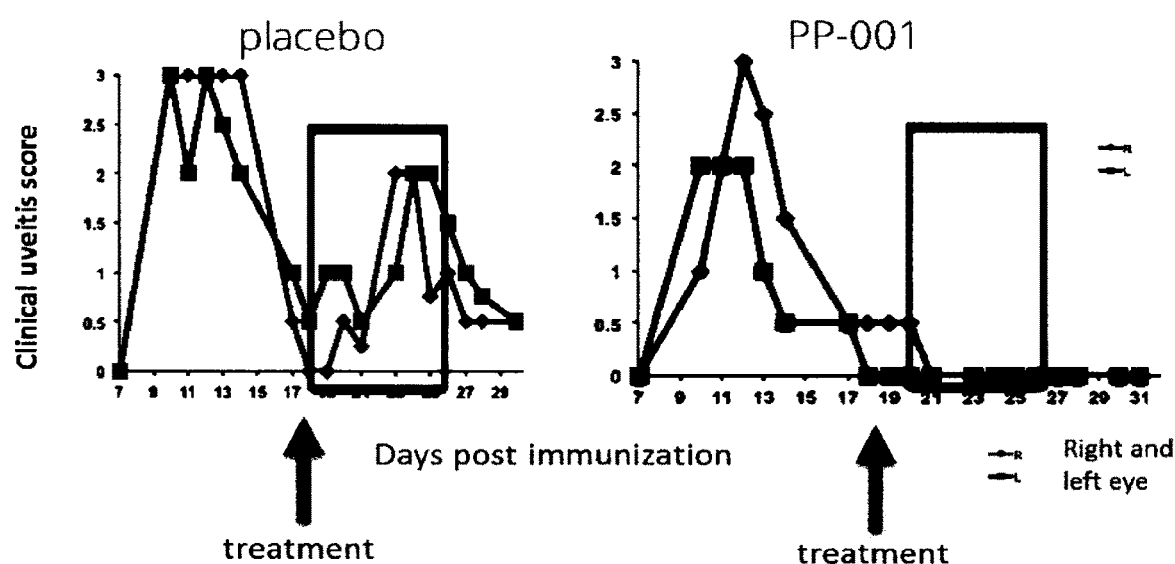
FIG. 1 shows a typical example of relapse development (uveitis score for left and right eye of one animal shown)

Furthermore not only the number of relapses was inhibited after administration of a DHODH inhibitor but also the time to the appearance of the first relapse was delayed in the treatment group compared to the placebo group. FIG. 1 shows the percentage of relapses after single intravitreal treatment with placebo or PP-001.

Example 3: Inhibition of Choroidal Neovascularization

Choroidal neovascularization is a known feature of posterior uveitis and a major cause of retinal destruction and loss of vision. To monitor the effect of PP-001 on neovascularization, the EAU model in Lewis rats was used.

In Lewis rats the disease was induced by immunizing animals with retinal antigen PDSAg, a 14 mer derived from S—Ag. Immunization with that peptide emulsified in Complete Freund's Adjuvant (CFA) leads to severe inflammation of the anterior chamber of the eyes and destruction of the retinal architecture and choroidal neovascularization Induction with PDSAg causes a monophasic disease with first clinical signs of inflammation observed between day 8 and 12 after immunization and reaching the peak of disease between day 14 and 18. Inflammation in the anterior chamber subsides until day 21 to 22 post immunization. Long term effects such as choroidal neovascularization are seen at the later stages of the disease after the inflammation of the anterior chamber has subsided. 18 Lewis rats were immunized with PDSAg. Starting at the beginning of the disease (day 9 post immunization) 6 animals were treated with PP-001 and 6 animals were treated with vehicle control. Starting at day 15 (peak of the disease) 6 additional animals were treated with PP-001. Post day 25 experiment was stopped and 12 eyes for each treatment group were histological analyzed for the presence of choroidal neovascularizations.

PP-001 reduced the number of choroidal neovascularizations by a factor of 3 ($p<0.005$) when treatment was started at the beginning of uveitis (day 9). When treatment started at day 15 PP-001 reduced the mean number of choroidal neovascularizations from 6 to 3 ($p<0.05$).

Example 4: Analysis of the Effect of PP-001 on the Cellular Protein Expression of Vascular Endothelial Growth Factor in EAU Rat Model for Uveitis Rats were immunized with 25 µg of the respective peptide as previously described.

After 10 to 12 days popliteal, inguinal and para-aortal lymph nodes (LN) were collected, single cell suspensions were stimulated with the respective antigen peptides at a final concentration of 10 µg/ml RPMI1640, supplemented with Penicillin/Streptomycin, L-Glutamine, essential and non-essential amino acids (all 4 from PAA, Colebee, Germany), 12.5 µM MeOH and 1% normal rat serum. After 3 days the cells were expanded in culture medium supplemented with 10% spleen conditioned medium (from Concanavalin A-stimulated rat spleen cells) and 5% fetal calf serum (FCS) for 4 days.

For restimulation $0.5-2 \times 10^6$ T cells/ml were incubated with irradiated (8 Gy) rat thymocytes (3-10 fold more than T cells) as antigen-presenting cells (APC) and 10 µg/ml of the specific antigen peptide in culture medium as described for the first stimulation. After two days of culturing cells were expanded with conditioned medium for 5 days as described above, followed by another cycle of restimulation and expansion.

To determine the effect of PP-001 on the protein expression of cytokines such as VEGF in vitro, the test substance was added to the cultures during the first, second and third stimulation with antigen (primary stimulation: $2 \times 10^6$ LN cells, no addition of antigen presenting cells (APC) necessary; $2^{nd}/3^{rd}$ restimulation: $0.5 \times 10^6$ T cells and $2.5 \times 10^6$ irradiated thymocytes per ml; 20 µg of the respective antigen peptide/ml).

PP-001 dissolved in DMSO was added to final concentrations of 3 µM, 10 µM and 30 µM to triplicate microwell cultures of 100 µl (final volume). After 24 h supernatants were collected and were subjected to a commercially available rat multiplex cytokine assay using the Luminex platform.

All concentration of PP-001 reduced the protein expression of VEGF.

Example 5: In Vivo Efficacy of PP-001 Eye Drops in an Experimental Adenoviral Ocular Infection in New Zealand White Rabbits 25 New Zealand White rabbits were inoculated in both eyes following general anesthesia with ketamine and xylazine, topical anesthesia with proparacaine, and corneal scarification (12 cross-hatched strokes of a #25 needle) with 50 µl of $3.0 \times 10^7$ PFU/ml ($1.5 \times 10^6$ PFU/eye) of Ad5 McEwen (Stock Jan. 17, 2008, $4.08 \times 10^8$ PFU/ml). Eyes were closed and gently rubbed for 5 seconds to ensure contact of the virus on all ocular surfaces.

At least 3 h after inoculation, all eyes were cultured for virus. Following topical anesthesia with proparacaine, a single cotton-tipped swab was placed into the lower fornix of each eye, rolled over the cornea into the upper fornix to recover adenovirus from the tear film and corneal and conjunctival surfaces. The swabs from each eye were placed individually into tubes containing 1 ml of outgrowth media and were frozen at $-70°$ C. pending plaque assay.

On day 1, the rabbits were divided into 5 treatment groups outlined in the chart below. The five treatment groups consisted of a vehicle control, 0.16% PP-001 8 times, 6 times, and 4 times daily for 10 days, and the positive antiviral control 0.5% cidofovir (CDV).

TABLE 1

| Group | Drug | Treatment Regimen | n Rabbits | n Eyes | Rabbit Numbers |
|---|---|---|---|---|---|
| PP-001-3 | 0.16% PP-001 | 8 times daily for 10 days | 5 | 10 | 1-5 |
| PP-001-2 | 0.16% PP-001 | 6 times daily for 10 days | 5 | 10 | 6-10 |
| PP-001-1 | 0.16% PP-001 | 4 times daily for 10 days | 5 | 10 | 11-15 |
| Vehicle | Placebo | 8 times daily for 10 days | 5 | 10 | 16-20 |
| CDV | 0.5% Cidofovir | 2 times daily for 7 days | 5 | 10 | 21-25 |

Begin of treatment on day 1. Drops were administered with at least a 45 min interval between drops. All eyes from all groups were cultured for virus on days 1, 3, 4, 5, 7, 9, 11, and 14 PI at least 1 h after the final doses of the treatments described above. At various times during the course of the experiment, Ad5 titers were determined on A549 cell monolayers using standard plaque assays. The ocular cultures to be titered were thawed, diluted (1:10) and inoculated onto A549 monolayers. The virus was adsorbed for 3 h. Following adsorption, 1 ml of media plus 0.5% methylcellulose was added to each well, and the plates were incubated at 37° C. in a 5% $CO_2$-water vapor atmosphere. After 7 days incubation, the cells were stained with 0.5% gentian violet, and the number of plaques were counted under a dissecting microscope (25×). The viral titers were then calculated, and expressed as plaque-forming units per milliliter (PFU/ml).

Preparation of Eye Drop Solutions:

Vehicle control eye drops: A solution containing 20 mg/ml polyvinyl-pyrrolidone, 10 mg/ml glycerol 85%, 2 mg/ml hydroxypropyl methylcellulose in sodium phosphate buffer adjusted to pH 7.

PP-001 eye drops: A solution containing 1.6 mg/ml PP-001, 20 mg/ml polyvinylpyrrolidone, 10 mg/ml glycerol 85%, 2 mg/ml hydroxypropyl methylcellulose in sodium phosphate buffer adjusted to pH 7.

Positive control cidofovir eye drops: 450 µl (33.75 mg) of the 75 mg/ml Cidofovir Injection (Mylan Institutional LLC, Rockford, IL Lot #130628, Exp. May 2015) was added to 6.3 ml of 0.9% sodium chloride for injection USP (Baxter Healthcare Corp. Deerfield, IL) to yield the 6.75 ml of 0.5% cidofovir.

In the current study, it was demonstrated that 0.16% PP-001 appears to be a safe and efficacious topical antiviral agent in the Ad5/NZW rabbit ocular model.

The antiviral efficacy of 0.16% PP-001 instilled 8 times and 6 times per day for 10 days was similar to the positive antiviral control, 0.5% cidofovir, instilled twice daily for 7 days (see FIG. 5).

There is a dose response with 0.16% PP-001. 0.16% PP-001 instilled 8 times and 6 times per day for 10 days was more efficacious than 0.16% PP-001 instilled 4 times per day for 10 days.

Example 6: Evaluation of Topical Administrations of PP-001 in a Controlled-Environment Chamber Murine Model of Dry Eye The aim of the study was to evaluate the tolerability and therapeutic potential of PP-001 in a murine model of dry eye syndrome.

Dry eye symptoms were induced in forty (40) pigmented C57BL/6N mice by exposing them to a controlled environment (relative humidity<25%, air-flow 15 L/min, temperature 20-22° C.) and systemic scopolamine administration (0.5 mg/72 h) for 10 days.

Mice were randomized into 4 groups of 10 animals and treated with PP-001, Restasis®, placebo and the forth group remained untreated.

Tear production and corneal defects were evaluated on days 3, 7 and 10 using phenol red thread and fluorescence staining in each of the four groups.

Preparation of Eye Drop Solutions:

Placebo eye drops: A solution containing 20 mg/ml polyvinylpyrrolidone, 10 mg/ml glycerol 85%, 2 mg/ml hydroxypropyl methylcellulose in sodium phosphate buffer adjusted to pH 7.

PP-001 eye drops: A solution containing 1.6 mg/ml PP-001, 20 mg/ml polyvinylpyrrolidone, 10 mg/ml glycerol 85%, 2 mg/ml hydroxypropyl methylcellulose in sodium phosphate buffer adjusted to pH 7.

Positive control: Restasis® (cyclosporine ophthalmic emulsion from Allergan)

All treatments were well tolerated and no changes in body weight were observed.

In all animal groups, corneal staining scores and tear productions were significantly altered on days 3, 7 and 10, in comparison to baseline values i.e. increasing of the corneal staining and reduction of tear production, except for Placebo group on day 7 on tear production.

Multiple instillations of Restasis® 0.05% reduced significantly corneal staining on Days 7 and 10, in comparison to the induced untreated group.

Multiple instillations of PP-001 reduced significantly corneal staining on Day 10, in comparison to the induced untreated group.

PP-001 and Restasis®0.05% reduced corneal staining on Day 10 when compared to placebo treatment.

Under said experimental conditions, multiple topical administrations of PP-001 1.6 mg/mL were well tolerated and showed reduced corneal surface damage comparable to Restasis® (see FIG. 6).

Example 7: Pharmacokinetic and Tolerability of Intravitreal Injections of PP-001 Solutions in Dutch Belted Rabbits 36 male Dutch Belted rabbits were divided in 4 groups: 16 animals each in group 1 and 2 received 0.0625 mg and 0.125 mg PP-001 per eye, 4 animals were administered with dose vehicle (sucrose solution) only. At designated time points animals were sacrificed and vitreous humor, retina, and choroid were collected from both eyes of each animal and weighed. Samples were analysed for PP-001 concentration using a specific HPLC/MS/MS analytical method and PK parameters were calculated with Phoenix WinNonlin software (v6.3) using a non-compartmental model with sparse sampling.

TABLE 2

| Group | Dose Route (OU) | Test Article | Dose | Dose Conc. | Dose Volume | Dose Vehicle | Termination Time Points |
|---|---|---|---|---|---|---|---|
| 1 | IVT | PP-001 | 0.0625 mg/eye | 2.5 mg/ml | 25 µL per eye | Sucrose solution (270 mOsm, pH 7-8) | 1, 2, 4, 8, 12, 24, 48, and 96 h post administration |
| 2 | IVT | PP-001 | 0.125 mg/eye | 5 mg/ml | 25 µL per eye | Sucrose solution (270 mOsm, pH 7-8) | 1, 2, 4, 8, 12, 24, 48, and 96 h post administration |

Animals were anesthetized with an intramuscular injection of ketamine hydrochloride (30 mg/kg) and xylazine (5 mg/kg) for the injection procedure.

The study director performed the IVT injection in both eyes (OU). Topical ocular anesthetics were used per ASI SOPs.

The eyes and surrounding tissues were cleaned and disinfected with 2% betadine ophthalmic solution and then rinsed with basic salt solution (BSS). Using a 30 gauge needle with length no greater than ⅝ inch, injections were made 5 to 7 mm from the limbus (where the cornea meets the sclera). Once inserted, the PP-001 or vehicle control was injected at a volume of 25 μL per eye. The needle was then removed and the eye rinsed with BSS.

The PP-001 was successfully administered via intravitreal injection in both eyes of 36 male Dutch Belted rabbits. No general health observations were noted for the duration of the study.

Overall, PP-001 appeared to be well tolerated and did not have any significant effect on the retinal and choroidal tissue under the conditions of this study.

Vitreous humor and choroid/sclera/retina were collected from both eyes of each animal at the designated time point and analyzed for PP-001 concentration using a specific HPLC/MS/MS analytical method.

Pharmacokinetic Parameters for PP-001 in Vitreous Humor and Choroid after Intravitreal Administration in Male Dutch Belted Rabbits

TABLE 3

| Pharmacokinetic Parameters | Group 1 (0.0625 mg/eye) | | Group 2 (0.125 mg/eye) | |
|---|---|---|---|---|
| | Vitreous Humor | Choroid | Vitreous Humor | Choroid |
| $C_{max}$ (μg/g) | 25.7 | 33.2 | 61.5 | 56.9 |
| $t_{1/2}$ (h) | 14.3 | 14.5 | 21.4 | 13.1 |
| $AUC_\infty$ (h · μg/g) | 294 | 270 | 802 | 1010 |

$C_{max}$: maximum plasma concentration;
$t_{1/2}$: half-life;
$AUC_\infty$: area under the curve, extrapolated to infinity

The invention claimed is:

1. A method for treating an ocular disease with a hydroorotate dehydrogenase (DHODH) inhibitor compound, wherein the compound is 3-(2,3,5,6-tetrafluoro-3'-trifluoromethoxy-biphenyl-1-ylcarbamoyl)-thiophene-2-carboxylic acid and is represented by the following formula:

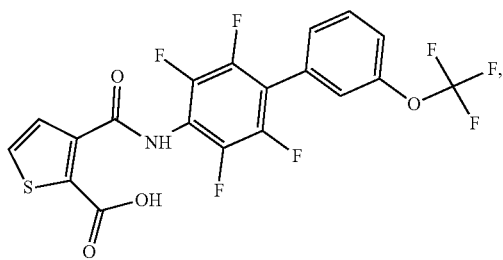 [SMILES: O=C(Nc1c(F)c(F)c(-c2cccc(OC(F)(F)F)c2)c(F)c1F)c1ccsc1C(=O)O]

comprising administering by intravitreal injection a therapeutically effective amount of the compound to a subject in need thereof.

2. The method according to claim 1, wherein the ocular disease is uveitis, dry eye, age-related macular degeneration (AMD), optic neuritis, retrobulbar neuritis, ocular inflammation or discomfort or trauma caused by or associated with the use of contact lenses, ocular inflammation, discomfort or trauma caused by or associated with the use of contact lenses, ocular inflammation, discomfort or trauma caused by or associated with refractive surgery, blepharitis, an optic nerve disease or disorder, or a conjunctivitis condition.

3. The method according to claim 2, wherein the conjunctivitis condition is keratitis, keratoconjunctivitis, vernal keratoconjunctivitis (VKC), or atopic keratoconjunctivitis (AKC).

4. The method according to claim 1, wherein the subject is suffering from uveitis, dry eye, age-related macular degeneration (AMD), or conjunctivitis.

5. The method according to claim 4, wherein the subject is suffering from age-related macular degeneration (AMD).

6. The method according to claim 1, wherein the ocular disease is caused by an adenovirus.

7. The method according to claim 1, wherein said compound is administered to the subject at least once per day.

8. The method according to claim 1, wherein said compound is administered at least once per month.

9. The method according to claim 1, wherein the compound is formulated with a pharmaceutically acceptable excipient.

10. The method according to claim 9, wherein the excipients are selected from the group consisting of hydrophilic polymer excipients, tonicity agents, buffers, sugars, preservatives, solvent and antioxidants.

11. The method according to claim 1, wherein the compound is administered in a form selected from a sterile eye drop formulation, a suspension, an emulsion, a microsphere formulation, and a sterile solution.

12. The method of claim 1, wherein the compound is formulated with an ophthalmically acceptable excipient.

13. The method according to claim 7, wherein the compound is administered in the range of from about one to about eight times a day.

14. The method according to claim 1, wherein the compound is administered to the posterior segment of the eye.

15. The method according to claim 1, wherein the compound is administered at least every six months.

16. The method according to claim 10, wherein the sugars are selected from the group consisting of trehalose, mannose, D-galactose, and lactose.

* * * * *